(12) United States Patent
Kobayashi et al.

(10) Patent No.: US 8,563,765 B2
(45) Date of Patent: Oct. 22, 2013

(54) DIAMINO ACID DERIVATIVE STARTING MATERIAL, MANUFACTURING METHOD THEREOF, AND DIAMINO ACID DERIVATIVE MANUFACTURING METHOD

(75) Inventors: Shu Kobayashi, Tokyo (JP); Yasuhiro Yamashita, Tokyo (JP); Kazutaka Seki, Saitama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 354 days.

(21) Appl. No.: 12/922,008

(22) PCT Filed: Feb. 27, 2009

(86) PCT No.: PCT/JP2009/053681
§ 371 (c)(1),
(2), (4) Date: Dec. 3, 2010

(87) PCT Pub. No.: WO2009/113409
PCT Pub. Date: Sep. 17, 2009

(65) Prior Publication Data
US 2011/0071310 A1 Mar. 24, 2011

(30) Foreign Application Priority Data
Mar. 10, 2008 (JP) .................................. 2008-058993

(51) Int. Cl.
*C07C 229/00* (2006.01)
(52) U.S. Cl.
USPC ........................................................ 560/37
(58) Field of Classification Search
USPC .................................................... 560/37, 15
See application file for complete search history.

(56) References Cited

PUBLICATIONS

Kobayashi et al. The Fluorenone Imines of Glycine Esters and their Phosphonic Acid Analogues, Angew.Chem Int. Ed.Online date Jun. 20, 2008, 47, 5613-5615.*
International Search Report issued Jun. 2, 2009 in PCT/JP09/53681 filed Feb. 27, 2009.
Zaragoza, Florencio, "Remarkable substituent effects on the chemoselectivity of rhodium (II) carbenoids derived from N-(2-diazo-3-oxobutyryl)-L-phenylalanine esters," Tetrahedron, vol. 51, No. 32, pp. 8829-8834, (1995).
Bradamante, Silvia et al., "249. Activated C, H-acids: N-alkyl-9-fluorenimines," Helvetica Chimica Acta, vol. 64, No. 8, pp. 2524-2527, (1981).
Viso, Alma et al., "α,β-Diamino Acids: Biological Significance and Synthetic Approaches," Chem. Rev., vol. 105, pp. 3167-3196, (Jul. 19, 2005).
Lucet, Denis et al., "The Chemistry of Vicinal Diamines," Angew. Chem. Int. Ed., vol. 37, pp. 2580-2627, (1998).
Soloshonok, Vadim A., "Highly Diastereoselective aza-Aldol Reactions of a Chiral Ni (II) Complex of Glycine with Imines. An Efficient Asymmetric Approach to 3-Perfluoroalkyl-2,3-Diamino Acids," Tetrahedron Letters, vol. 38, No. 26, pp. 4671-4674, (1997).
Demong, Duane E., et al., "The asymmetric synthesis of (2S,3R)-capreomycidine," Tetrahedron Letters, vol. 42, pp. 3529-3532, (2001).
Demong, Duane E., et al., "Asymmetric Synthesis of (2S,3R)-Capreomycidine and the Total Synthesis of Capreomycin IB," J. Am. Chem. Soc., vol. 125, pp. 8561-8565, (2003).
Viso, Alma et al., "Sulfur-Directed Asymmetric 1,3-Dipolar Cycloadditions of Azomethine Ylides with Enantiopure Sulfinimines," J. Org. Chem., vol. 62, pp. 2316-2317, (1997).
Viso, Alma et al., "Lewis Acid Catalyzed Condensation between Glycine Iminoester Enolates and p-Tolylsulfinimines," Synlett, No. 10, pp. 1543-1546, ISSN: 0936-5214, (1999).
Fernandez De La Pradilla, Roberto et al., "Synthesis of Enantiopure 1-Benzyl-2,3-disubstituted Piperazines from Enantiopure p-Toluenesulfinimines," Synlett, No. 5, pp. 755-758, ISSN: 0936-5214, (2002).
Viso, Alma et al., "Highly Diastereoselective [3+2] Cycloadditions between Nonracemic p-Tolylsulfinimines and Iminoesters: An Efficient Entry to Enantiopure Imidazolidines and Vicinal Diaminoalcohols," Chem. Eur. J., vol. 9, pp. 2867-22876, (2003).
Viso, Alma et al., "Fine-Tuned Aminal Cleavage: A Concise Route to Differentially Protected Enantiopure syn-α,β-Diamino Esters," J. Org. Chem., vol. 69, pp. 1542-1547, (Jan. 27, 2004).
Davis, Franklin A., et al., "Asymmetric Synthesis of syn-(2R,3S)- and anti-(2S,3S)-Ethyl Diamino-3-phenylpropanoates from N-(Benzylidene)-p-toluenesulfinamide and Glycine Enolates," Organic Letters, vol. 6, No. 16, pp. 2789-2792, (Jul. 7, 2004).
Davis, Franklin A., et al., "Asymmetric Total Synthesis of (–)-Agelastatin A Using Sulfinimine (N-Sulfinyl Imine) Derived Methodologies," Organic Letters, vol. 7, No. 4. pages 621-623, (Jan. 20, 2005).
O'Donnell, Martin J., et al., "The Synthesis of Amino Acids by Phase-Transfer Reactions," Tetrahedron Letters, No. 30, pp. 2641-2644, (1978).
O'Donnell, Martin J., et al., "The Synthesis of Amino Acid Derivatives by Catalytic Phase-Transfer Alkylations," Tetrahedron Letters, No. 47, pp. 4625-4628, (1978).
Maruoka, Keiji et al., "Enantioselective Amino Acid Synthesis by Chiral Phase-Transfer Catalysis," Chem. Rev. vol. 103, pp. 3013-3028, (Jun. 13, 2003).
O'Donnell, Martin J., et al., "The Enantioselective Synthesis of α-Amino Acids by Phase-Transfer Catalysis with Achiral Schiff Base Esters," Accounts of Chemical Research, vol. 37, No. 8, pp. 506-517, (Jun. 5, 2004).
Lygo, Barry et al., "Asymmetric Phase-Transfer Catalysis Utilizing Chiral Quaternary Ammonium Salts: Asymmetric Alkylation of Glycine Imines," Accounts of Chemical Research, vol. 37, No. 8, pp. 518-525, (Jan. 28, 2004).
Hashimoto, Takuya et al., "Recent Development and Application of Chiral Phase-Transfer Catalysts," Chemicals Reviews, vol. 107, No. 12, pp. 5656-5682, (Dec. 12, 2007).

(Continued)

*Primary Examiner* — Johann R Richter
*Assistant Examiner* — Blaine G Doletski
(74) *Attorney, Agent, or Firm* — Oblon, Spivak, McClelland, Maier & Neustadt, L.L.P.

(57) ABSTRACT

Provided is an efficient technology for synthesizing diamino acids (diamino acid derivatives). Disclosed is a manufacturing method for diamino acid derivatives wherein the fluorenyl groups of the diamino acid derivative starting materials represented by General Formula [II] or [IV] are removed.

7 Claims, No Drawings

(56) References Cited

PUBLICATIONS

O'Donnell, Martin J., et al., "Acidities of Glycine Schiff Bases and Alkylation of Their Conjugate Bases," J. Am. Chem. Soc., vol. 110, No. 25, pp. 8520-8525, (1988).

Bernardi, Luca et al., "Catalytic Asymmetric Mannich Reactions of Glycine Derivatives with Imines. A New Approach to Optically Active α,β-Diamino Acid Derivatives," J. Org. Chem., vol. 68, No. 7, pp. 2583-2591, (Mar. 4, 2003).

Ooi, Takashi et al., "Catalytic Asymmetric Synthesis of a Nitrogen Analogue of Dialkyl Tartrate by Direct Mannich Reaction under Phase-Transfer Conditions," Organic Letters, vol. 6, No. 14, pp. 2397-2399, (Jun. 16, 2004).

Okada, Akihiro et al., "Enantio- and Diastereoselective Catalytic Mannich-Type Reaction of a Glycine Schiff Base Using a Chiral Two-Center Phase Transfer Catalyst," Angew. Chem. Int. Ed., vol. 44, pp. 4564-4567, (2005).

Shibuguchi, Tomoyuki et al., "Catalytic Asymmetric Phase-Transfer Michael Reaction and Mannich-Type Reaction of Glycine Schiff Bases with Tartrate-Derived Diammonium Salts," Chemistry Asian Journal vol. 2, pp. 794-801, (2007).

Kobayashi, Jun et al., "Direct Addition of Glycine Derivatives to Enamines," Chemistry Letters, vol. 34, No. 2, pp. 268-269, (2005).

Salter, Matthew M., et al., "Direct-Type Catalytic Three-Component Mannich Reactions Leading to an Efficient Synthesis of α,β-Diamino Acid Derivatives," Organic Letters, vol. 8, No. 16, pp. 3533-3536, (Jul. 1, 2006).

Ishikawa, Tsutomu et al., "Modified guanidines as chiral superbases: application to asymmetric Michael reaction of glycine imine with acrylate or its related compounds," Chem. Comm., pp. 245-246, (Jan. 18, 2001).

Matthews, Walter S., et al., "Equilibrium Acidities of Carbon Acids. VI. Establishment of an Absolute Scale of Acidities in Dimethyl Sulfoxide Solution," Journal of the American Chemical Society, vol. 97, No. 24, pp. 7006-7014, (Nov. 26, 1975).

Keefer, Larry K., et al., "The 9-Fluorenylmethoxycarbonyl Function, a New Base-Sensitive Amino-Protecting Group," Journal of the American Chemical Society, vol. 92, No. 19, pp. 5748-5749, (Sep. 23, 1970).

Carpino, Louis A., et al., "The 9-Fluorenylmethoxycarbonyl Amino-Protecting Group," J Org. Chem., vol. 37, No. 22, pp. 3404-3409, (1972).

O'Donnell, Martin J., et al., "A Mild and Efficient Route to Schiff Base Derivatives of Amino Acids," J. Org. Chem., vol. 47, No. 13, pp. 2663-2666, (1982).

O'Donnell, Martin J., et al., "Preparation of an α-Aminophosphonate Cation Equivalent and its Reaction with Organoboranes," Tetrahedron Letters, vol. 35, No. 35, pp. 6421-6424, (1994).

Genet, J.P. et al., "Synthesis of Diethyl (1-Aminoalkyl)phosphonates Under Solid-Liquid Phase-Transfer Catalysis Conditions," pp. 41-43, (Jan. 1990).

Kim, Dae Young et al., "Michael Addition of N-(Diphenylmethylene)-Aminomethylphosphonate to Acrylates Using Phase Transfer Catalysis Conditions: Synthesis of 1-(N-Diphenylmethylene)Amino-3-(Alkoxycarbonyl)-Propylphosphonates," Synthetic Communications, vol. 31, No. 21, pp. 3315-3322, (Sep. 30, 2001).

Jaszay, Zsuzsa M., et al., "Catalytic enantioselective Michael addition in the synthesis of α-aminophosphonates," Tetrahedron: Asymmetry, vol. 16, pp. 3837-3840, (2005).

Blaszczyk, Roman et al., "Direct synthesis of protected diethyl 1,2-diaminoalkylphosphonates," Tetrahedron Letters, vol. 48, pp. 5859-5863, (2007).

Takamura, Masahiro et al., "A Catalytic Asymmetric Strecker-Type Reaction: Interesting Reactivity Difference between TMSCN and HCN," Angew. Chem. Int. Ed., vol. 39, No. 9, pp. 1650-1662, (2000).

Luca Bernardi, et al. "Catalytic Asymmetric Mannich Reactions of Glycine Derivatives with Imines. A New Approach to Optically Active a α-Diamino Acid Derivatives" J. Org. Chem, 2003, 68, 2583-2591.

\* cited by examiner

DIAMINO ACID DERIVATIVE STARTING MATERIAL, MANUFACTURING METHOD THEREOF, AND DIAMINO ACID DERIVATIVE MANUFACTURING METHOD

APPLICABLE FIELD IN THE INDUSTRY

The present invention relates to starting materials of diamino acid derivatives, a manufacturing method thereof, and a manufacturing method of diamino acid derivatives.

BACKGROUND ART

α, β-diamino acid is an important compound as a chemical product and a pharmaceutical product. The foregoing α, β-diamino acid has two asymmetric points in its backbone. And, asymmetric synthesis of the α, β-diamino acid is an important task to be studied/researched. By the way, the Mannich-type reaction (carbon-carbon bond forming reaction) between an α-anion equivalent of glycine and imine (or an imine equivalent) is the most efficient technique (Scheme 2-1-1). The reason is that the two asymmetric points being generated can be simultaneously controlled. Yet, the reason is that the α, β-diamino acid backbone having desired configurations can be structured at a time.

A typified example of the Mannich-type reactions using the α-anion equivalent of glycine is shown below.

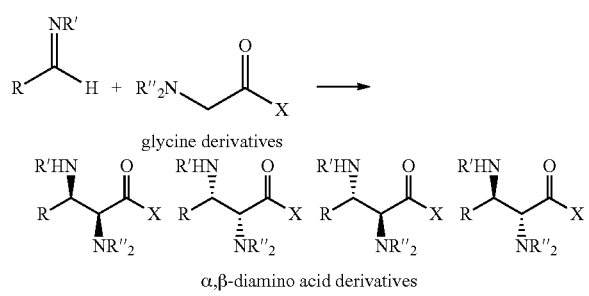

Scheme 2-1-1. Mannich-type reactions of glycine derivatives with imine equivalents Soloshonok, Avilov et al. reported the diastereoselective reaction using chiral auxiliaries (a stoichiometric amount of a chiral source). Optically active nickel composites derived from glycine are used for this reaction. And, the highly diastereoselective reaction was realized. The substrate generality is lacking. However, the product can be induced into syn α, β-diamino acid (Scheme 2-1-2).

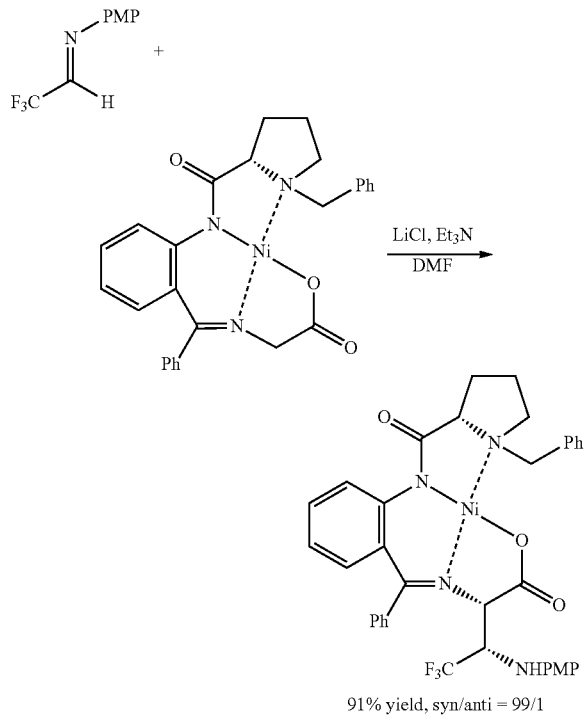

Scheme 2-1-2. Mannich-type reactions of chiral glycine derivatives

Williams et al. reported the diastereoselective reaction using glycine derivatives derived from chiral oxazinone. In any of these examples, the chiral source was introduced into the glycine derivatives, being a nucleophile.

Viso et al. and Davis et al. reported an example of introducing the chiral source into an electrophile (the reaction using chiral sulfinimine as a substituent on nitrogen).

Davis et al. can manufactures a syn-compound and an anti-compound at will by changing a protecting group on nitrogen of glycine derivatives (Scheme 2-1-3).

Scheme 2-1-3. Mannich-type reaction of chiral electrophiles

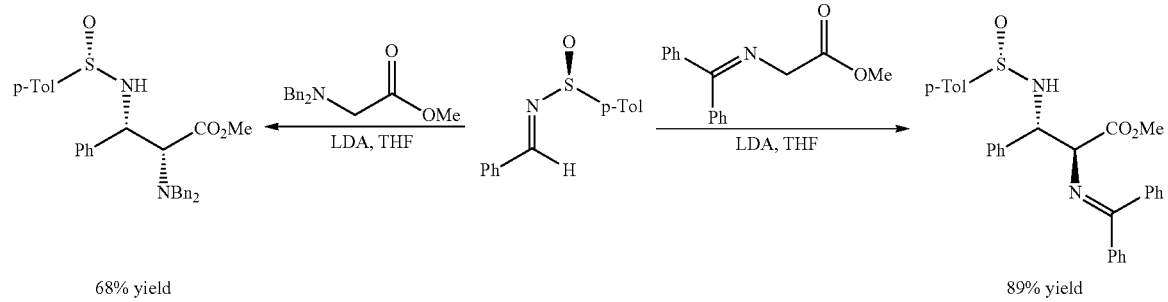

After O'Donnel et al. synthesized the glycine Schiff base derived from stable benzophenone, the various reactions using this substrate as prochiral glycine derivatives have been rapidly developed. The mono-alkylated products were obtained by using the glycine Schiff base derived from benzophenone. The mono-alkylated products are hardly obtained with the glycine Schiff base derived from aldimines. In addition, putting stability in water into practical use allowed a large number of optically active phase transfer catalysts to be developed. And, it has become possible to manufacture both of D and L-optically active amino acid derivatives at will (Scheme 2-1-4).

This glycine Schiff base derived from benzophenone (the pKa value of α-position hydrogen is approximately 18.7) is easily deprotonated with KOH that is used together with the phase transfer catalyst (Figure 2-1-1).

However, the dialkylation of the Schiff base derived from alanine is suppressed because the pKa value thereof is approximately 22.8.

The asymmetric Mannich-type reaction as well using this glycine Schiff base derived from benzophenone has been developed. Its example is shown below.

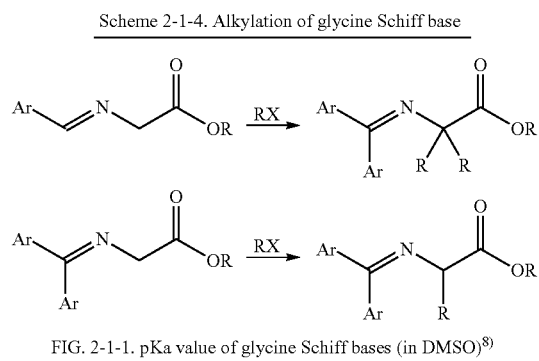

FIG. 2-1-1. pKa value of glycine Schiff bases (in DMSO)[8]

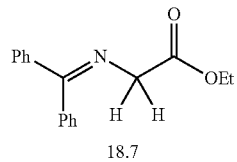

18.7

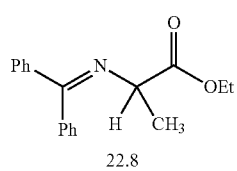

22.8

Jorgensen et al. reported the addition reaction to N-tosylimines using triethylamine as a base in the presence of a copper complex having a chiral ligand (Scheme 2-1-5).

Herein, effectiveness is demonstrated in not only aromatic imines but also imines derived from aliphatic aldehydes. In either case, the obtained α, β-diamino acid derivatives exhibits the high enantioselectivity. However, using the aromatic imines causes the diastereoselectivity to decline slightly. As a rule, it is difficult to remove a tosyl group, being a protecting group of the amino group.

Scheme 2-1-5.

Jorgensen, K. A. et al. (2003)

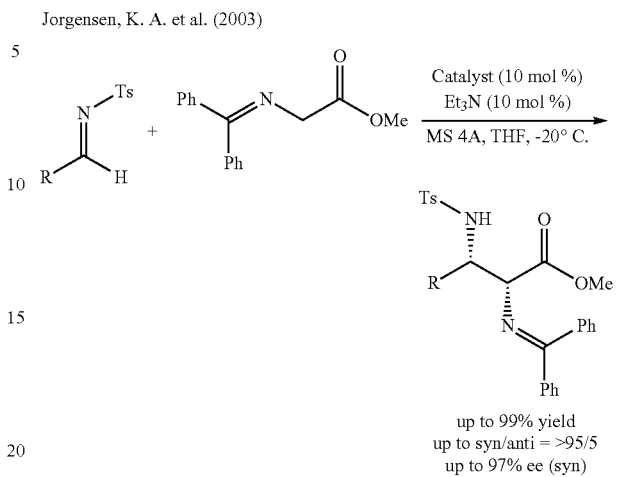

up to 99% yield
up to syn/anti = >95/5
up to 97% ee (syn)

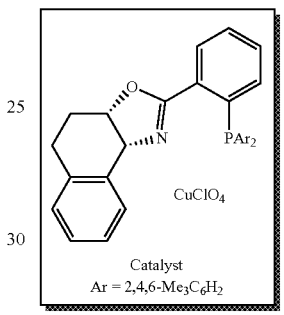

Catalyst
Ar = 2,4,6-Me$_3$C$_6$H$_2$

Maruoka et al. reported the various reactions (for example, the asymmetric alkylation of the glycine Schiff base derived from benzophenone) using the chiral phase transfer catalyst developed on their own. For example, the Mannich-type reaction for α-iminoester was reported (Scheme 2-1-6). This reaction affords 3-amino aspartic acid derivatives. However, the active α-iminoester has to be used as an electrophile. For this, the problem remains in terms of the substrate generality.

Scheme 2-1-6.

Maruoka, K. et al. (2004)

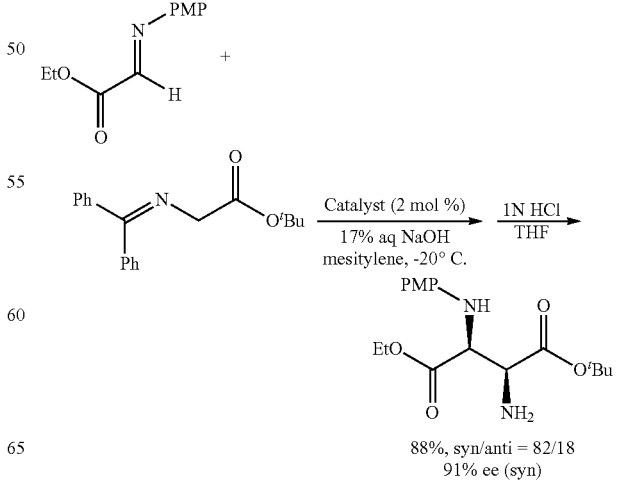

88%, syn/anti = 82/18
91% ee (syn)

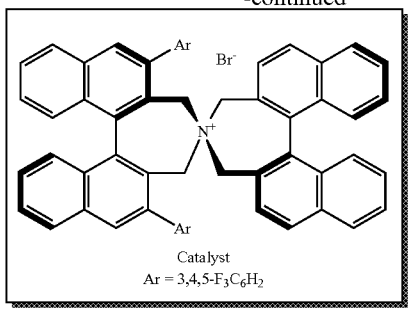

Catalyst
Ar = 3,4,5-F$_3$C$_6$H$_2$

Shibasaki et al. reported the Mannich-type reaction (the phase transfer catalyst: an optically active diammonium salt derived from tartaric acid) for N-Boc imine (Scheme 2-1-7). Not only the aromatic imines but also the imines derived from aliphatic aldehydes were reported herein. And, the wide-range substrate generality is shown. In this reaction, syn α, β-diaminoester derivatives are highly selectively obtained.

Scheme 2-1-7.

Shibasaki, M. et al. (2005, 2007)

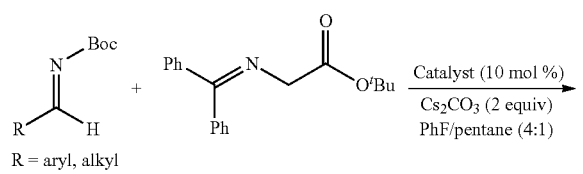

up to 96% yield
up to syn/anti = >99/1
up to 90% ee (syn)

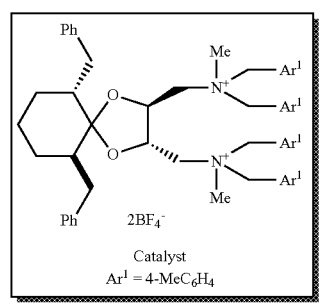

Catalyst
Ar$^1$ = 4-MeC$_6$H$_4$

This inventor et al. as well has studied the Mannich-type reaction using the glycine Schiff base (Scheme 2-1-8).

With this reaction, the deprotonation is conducted with enamine (having the Lewis acid activated glycine Schiff base as a substrate). And, enolate is generated. This reaction is a reaction of conducting a nucleophilic addition reaction for iminium that is co-generated (a reaction requiring no external base). Further, this inventor et al. conducted the development into the asymmetric reaction with Me-DUPHOS defined as a chiral ligand. This reaction has a problem that should be solved, namely, a problem of the diastereoselectivity. However, the obtained target product exhibits the high enantioselectivity. It was reported that applying this reaction to a three-component Mannich-type reaction allowed the obtained adduct to exhibit the high diastereoselectivity. In this reaction, the anti-product is obtained as a main product differently from the other Mannich-type reactions. And, it is of interest from a viewpoint of the reaction mechanism.

Scheme 2-1-8.

Kobayashi, S. et al. (2005, 2006)

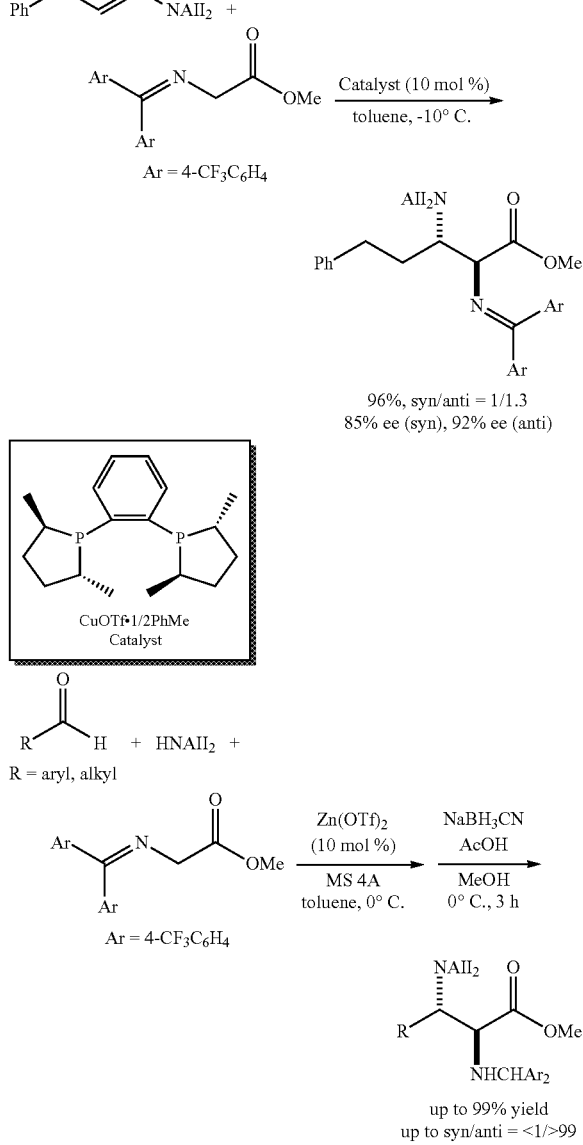

Above, examples of the reports of the catalytically asymmetric Mannich-type reactions using the glycine Schiff base derived from benzophenone were mentioned.

However, the room for further improvement is left hereto in terms of the selectivity, the substrate generality, etc.

One equivalent of the metal bases or more such as KOH used together with the phase transfer catalyst is used. Thus, the above reaction is not satisfactory as an environment-friendly reaction.

Jorgensen et al. reported that the deprotonation was difficult with a catalyst amount of organic amines (tertiary amines) (Scheme 2-1-9).

Scheme 2-1-9.

Jorgensen, K. A. et al (2003)

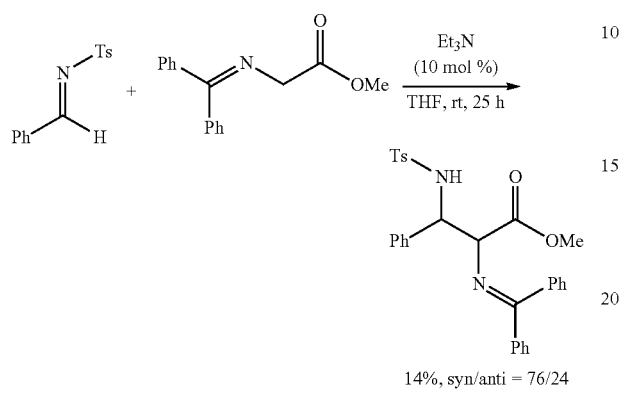

14%, syn/anti = 76/24

There are many reactions other than the Mannich-type reactions where the deprotonation is rate-limited. Ishikawa et al. reported the Michael reaction using chiral guanidine (Scheme 2-1-10). This reaction exhibits the high enantioselectivity. And, the catalyst is collected. However, the excessive substrate has to be used. Further, a progress of the reaction is slow. Thus, the development of the high reactive substrate is desired.

Scheme 2-1-10.

Ishikawa, T. et al.

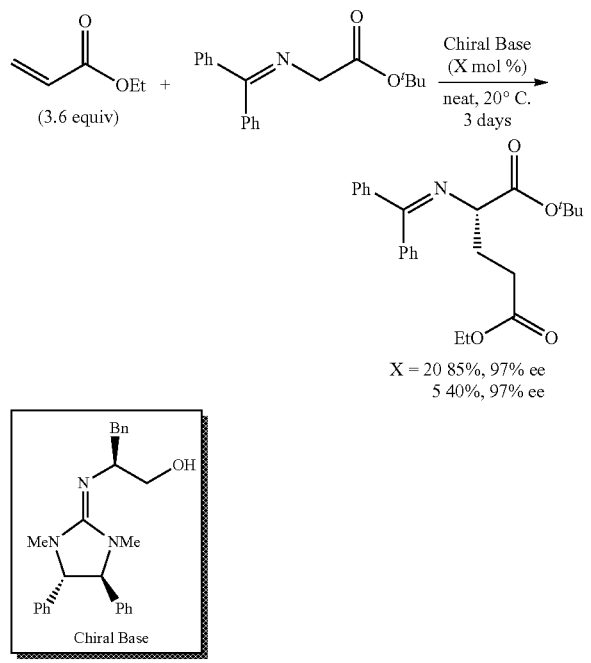

X = 20  85%, 97% ee
5   40%, 97% ee

Fluorene is more stable in terms of the conjugate base after the deprotonation as compared with diphenylmethane. And, acidity of the 9-position hydrogen is very high (Figure 2-1-2).

Carpino et al. reported a Fmoc group as a protecting group of the amino group by utilizing this properties. While this Fmoc group is not broken under the acid condition that is used at the moment of breaking a Boc group, it is easily broken with the relative weak base such as secondly amine. And, the Fmoc group is used in not only solid-phase synthesis of peptides but also synthesis of natural products because it is selectively deprotectable (Scheme 2-1-11).

This inventor thought that the reactivity of the substrate was able to be raised by utilizing a unique property that this methine anion is stable.

FIG. 2-1-2. pKa value in DMSO

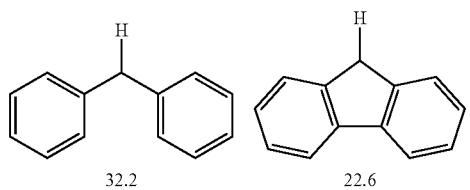

32.2                          22.6

Scheme 2-1-11.

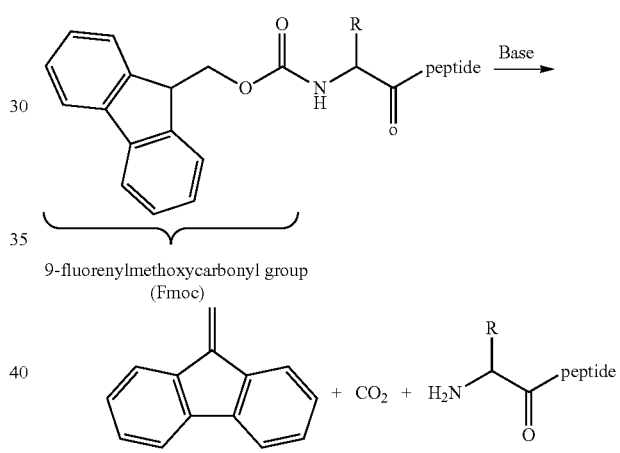

At first, a concept of the glycine Schiff base derived from fluorenone imine will be described.

α-position hydrogen of the glycine alkyl ester derived from benzophenone exhibits very high acidity as compared with α-position hydrogen of the general esters (Figure 2-1-3).

FIG. 2-1-3. pKa value of ester (in DMSO)

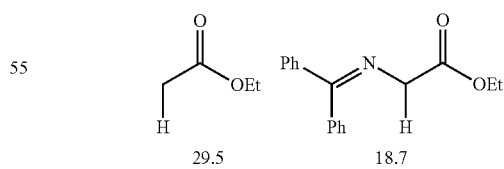

29.5                          18.7

This is owing to an electron withdrawing effect of the α-position Schiff base portion.

It is thought that the electron withdrawing of the Schiff base portion has a correlation with stability of a resonance structure of the methine anion.

Thereupon, this inventor used the glycine Schiff base derived from fluorenone (which is thought to be stable due to a contribution by the resonance structure having flatness, and having 14π-electron aromaticity) for the corresponding conjugate base. That is, it was thought that the glycine Schiff base derived from fluorenone promoted the deprotonation of the α-position hydrogen all the more, and developed the Mannich-type reaction more smoothly than the base derived from benzophenone (Figure 2-1-4).

FIG. 2-1-4. Concept of substrate design

As a matter of fact, as shown below, some reports say that the acidity of the α-position hydrogen of the fluorenone imine is very higher than that of the benzophenone imine (The former differs from the latter by approximately ten times in terms of the pKa value in a DMSO solution (Figure 2-1-5).

FIG. 2-1-5. pKa value of Schiff bases (in DMSO)

24.3    14.5

Non-patent document 1: Viso, A.; Fernandez de la Pradilla, R.; Garcia, A.; Flores, A. Chem. Rev. 2005, 105, 3167.
Non-patent document 2: Lucet, D.; Gall, T. L.; Mioskowski, C. Angew. Chem., Int. Ed. Engl. 1998, 37, 2580.
Non-patent document 3: Soloshonok, V. A.; Avilov, D. V.; Kukhar, V. P.; Meervelt, L. V.; Mischenko, N. Tetrahedron Lett. 1997, 38, 4671.
Non-patent document 4: DeMong, D. E.; Williams, R. M. Tetrahedron Lett. 2001, 42, 3529.
Non-patent document 5: DeMong, D. E.; Williams, R. M. J. Am. Chem. Soc. 2003, 125, 8561.
Non-patent document 6: Viso, A.; Fernandez de la Pradilla, R.; Guerrero-Strachan, C.; Alonso, M.; Martinez-Ripoll, M.; Andre, I. J. Org. Chem. 1997, 62, 2316.
Non-patent document 7: Viso, A.; Fernandez de la Pradilla, R.; Garcia, A.; Alonso, M.; Guerrero-Strachan, C.; Fonseca, I. Synlett 1999, 1543.
Non-patent document 8: Viso, A.; Fernandez de la Pradilla, R.; Lopez-Rodriguez, M. L.; Garcia, A.; Tortosa, M. Synlett 2002, 755.
Non-patent document 9: Viso, A.; Fernandez de la Pradilla, R.; Garcia, A.; Guerrero-Strachan, C.; Alonso, M.; Tortosa, M.; Flores, A.; Martinez-Ripoll, M.; Fonseca, I.; Andre, I.; Rodriguez, A. Chem. Eur. J. 2003, 9, 2867.
Non-patent document 10: Viso, A.; Fernandez de la Pradilla, R.; Lopez-Rodriguez, M. L.; Garcia, A.; Flores, A.; Alonso, M. J. Org. Chem. 2004, 69, 1542.
Non-patent document 11: Davis, F. A.; Deng, J. Org. Lett. 2004, 6, 2789.
Non-patent document 12: Davis, F. A.; Deng, J. Org. Lett. 2005, 7, 621.
Non-patent document 13: O'Donnel, M. J.; Boniece, J. M.; Earp, S. E. Tetrahedron Lett. 1978, 30, 2641.
Non-patent document 14: O'Donnel, M. J.; Eckrich, T. M. Tetrahedron Lett. 1978, 30, 4625.
Non-patent document 15: Maruoka, K.; Ooi, T. Chem. Rev. 2003, 103, 3013.
Non-patent document 16: O'Donnel, M. J. Acc. Chem. Res. 2004, 37, 506.
Non-patent document 17: Lygo, B.; Andrews, B. I. Acc. Chem. Res. 2004, 37, 518.
Non-patent document 18: Maruoka, K.; Hashimoto, T. Chem. Rev. 2007, 107, 5656.
Non-patent document 19: O'Donnel, M. J.; Bennett, W. D.; Bruder, W. A.; Jacobsen, W. N.; Knuth, K.; LeClef, B.; Plot, R. L.; Bordwell, F. G.; Mrozack, S. R.; Cripe, T. A. J. Org. Chem. 1988, 110, 8520.
Non-patent document 20: Bernardi, L.; Gothelf, A. S.; Hazell, R. G.; Jorgensen, K. A. J. Org. Chem. 2003, 68, 2583.
Non-patent document 21: Ooi, T.; Kameda, M.; Fujii, J.; Maruoka, K. Org. Lett. 2004, 6, 2397.
Non-patent document 22: Okada, A.; Shibuguchi, T.; Ohshima, T.; Masu, H.; Yamaguchi, K.; Shibasaki, M. Angew. Chem., Int. Ed. 2005, 44, 4564.
Non-patent document 23: Shibuguchi, T.; Mihara, H.; Kuramochi, A.; Ohshima, T.; Shibasaki, M. Chem. Asian J. 2007, 2, 794.
Non-patent document 24: Kobayashi, J.; Yamashita, Y.; Kobayashi, S. Chem. Lett. 2005, 34, 268.
Non-patent document 25: Salter, M. M.; Kobayashi, J.; Shimizu, Y.; Kobayashi, S. Org. Lett. 2006, 8, 3533.
Non-patent document 26: Ishikawa, T.; Araki, Y.; Kumamoto, T.; Seki, H.; Fukuda, K.; Isobe, T. Chem. Commun. 2001, 245.
Non-patent document 27: Matthews, W. S.; Bares, J. E.; Bartmess, J. E.; Bordwell, F. G.; Cornforth, F. J.; Drucker, G. E.; Margolin, Z.; McCallum, R. J.; Vanier, N. R. J. Am. Chem. Soc. 1975, 97, 7006
Non-patent document 28: Carpino, A. L.; Han, G. Y. J. Am. Chem. Soc. 1970, 92, 5748.
Non-patent document 29: Carpino, A. L.; Han, G. Y. J. Org. Chem. 1972, 37, 3404.
Non-patent document 30: O'Donnel, M. J.; Plot, R. L. J. Org. Chem. 1982, 47, 2663.
Non-patent document 31: O'Donnel, M. J.; Lawley, L. K.; Pushpavanam, P. B.; Burger, A.; Bordwell, F. G.; Zhang, X. Tetrahedron Lett. 1994, 35, 6421

Non-patent document 32: Genet, J. P.; Uziel, J.; Touzin, A. M.; Juge, S. Synthesis 1990, 41.

Non-patent document 33: Kim, D. Y.; Suh, K. H.; Huh, S. C.; Lee, K. Synth. Commun. 2000, 31, 3315.

Non-patent document 34: Jaszay, Z. M.; Nemeth, G.; Pham, T. S.; Petnehazy, I.; Grun, A.; Toke, L. Tetrahedron Asymmetry 2005, 16, 3837.

Non-patent document 35: Blaszczyk, R.; Gajda, T. Tetrahedron Lett. 2007, 48, 5859.

Non-patent document 36: Takamura, M.; Hamashima, Y.; Usuda, H.; Kanai, M.; Shibasaki, M. Angew. Chem., Int. Ed. 2000, 39, 1650.

DISCLOSURE OF THE INVENTION

Problems to be Solved by the Invention

By the way, with conventional proposed arts, the diamino acid derivatives cannot be efficiently obtained.

Thus, a task that the present invention is to solve, that is, an object of the present invention is to provide a technology for efficiently synthesizing the diamino acids (diamino acid derivatives (derivatives such as diamino acid ester and diamino phosphonic acid ester)).

Means for Solving the Problem

The foregoing problems are solved by a manufacturing method of starting materials of diamino acid derivatives represented by the following general formula [II] that is characterized in reacting a compound represented by the following general formula [I] with a compound represented by the following general formula [V].

The foregoing problems are solved by a diamino acid derivative starting material that is characterized in being a compound represented by the following general formula [I].

The foregoing problems are solved by a diamino acid derivative starting material that is characterized in being a compound represented by the following general formula [II].

The foregoing problems are solved by a manufacturing method of diamino acid derivatives that is characterized in removing a fluorenyl group of the diamino acid derivative starting material represented by the following general formula [II].

The foregoing problems are solved by a manufacturing method of starting materials of diamino acid derivatives represented by the following general formula [IV] that is characterized in reacting a compound represented by the following general formula [III] with a compound represented by the following general formula [V].

The foregoing problems are solved by a diamino acid derivative starting material that is characterized in being a compound represented by the following general formula [III].

The foregoing problems are solved by a diamino acid derivative starting material that is characterized in being a compound represented by the following general formula [IV].

The foregoing problems are solved by a manufacturing method of diamino acid derivatives that is characterized in removing a fluorenyl group of the diamino acid derivative starting material represented by the following general formula [IV].

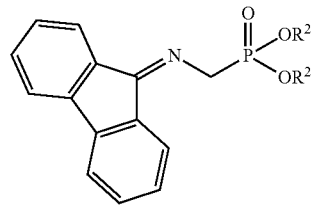

General formula [I]

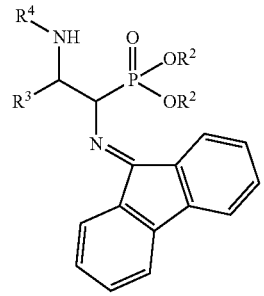

General formula [II]

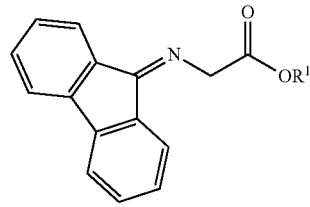

General formula [III]

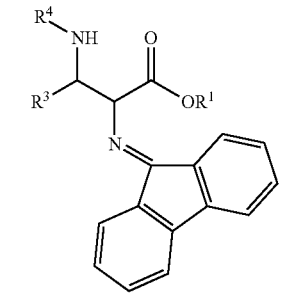

General formula [IV]

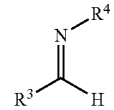

General formula [V]

The foregoing $R^1$ is a substituted hydrocarbon group or an unsubstituted hydrocarbon group.

The foregoing $R^2$ is a substituted hydrocarbon group or an unsubstituted hydrocarbon group. All of $R^2$ may be identical to each other, and may differ from each other.

The foregoing $R^3$ is a substituted hydrocarbon group, a substituted heterocyclic group, an unsubstituted hydrocarbon group, or an unsubstituted heterocyclic group.

The foregoing $R^4$ is an electron-withdrawing group.

The foregoing fluorenyl group is a ring-substituted fluorenyl group or a ring-unsubstituted fluorenyl group.

An Advantageous Effect of the Invention

The compounds of the general formula [II] or the general formula [IV] can be efficiently obtained because the compounds of the general formula [I] or the general formula [III] having the fluorenyl group are used.

In particular, a catalyst amount of the base allows the reaction to progress.

Further, the asymmetric reaction is also possible.

And, for example, the derivatives such diamino acid ester and diamino phosphonic acid ester can be efficiently obtained. The diamino acid derivatives are efficiently obtained by thereafter removing the fluorenyl group.

BEST MODE FOR CARRYING OUT THE INVENTION

The present invention relates to diamino acid derivative starting materials. The foregoing starting material is a compound represented by the foregoing general formula [I]. Or the foregoing starting material is a compound represented by the foregoing general formula [II]. Or the foregoing starting material is a compound represented by the foregoing general formula [III]. Or the foregoing starting material is a compound represented by the foregoing general formula [IV].

The present invention relates to a manufacturing method of diamino acid derivative starting materials. The foregoing method is a method of reacting the compound represented by the foregoing general formula [I] with the compound represented by the foregoing general formula [V]. Or, the foregoing method is a method of reacting the compound represented by the foregoing general formula [III] with the compound represented by the foregoing general formula [V]. Using an optically active basic catalyst at the moment of the reaction between each of the foregoing compound [I] and the foregoing compound [III] and the foregoing compound [V] allows the optically active diamino acid derivative starting material to be obtained. As the foregoing catalyst, for example, an optically active guanidine compound can be listed. Or, an optically active basic catalyst configured using $MX_2$ (M is Be, Mg, Ca, Sr, Ba, or Ra. X is an arbitrary group) and the compound represented by the following general formula [VI] can be listed. And, a catalyst amount of the base allows the reaction to progress.

General formula [VI]

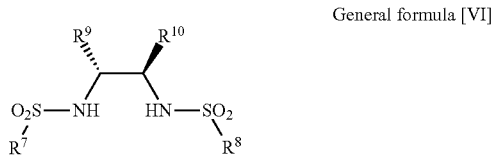

[$R^7$, $R^8$, $R^9$, and $R^{10}$ each represents a substituted cyclic group or an unsubstituted cyclic group. $R^9$ and $R^{10}$ form a ring in some cases, and they do not form a ring in some cases.]

The present invention relates to a manufacturing method of diamino acid derivatives. The foregoing method is a method of removing the fluorenyl group of the diamino acid derivative starting material represented by the foregoing general formula [II]. Or the foregoing method is a method of removing the fluorenyl group of the diamino acid derivative starting material represented by the foregoing general formula [VI]. The foregoing fluorenyl group is preferably removed with an acid process.

The foregoing $R^1$ is a substituted hydrocarbon group or an unsubstituted hydrocarbon group. The preferable $R^1$ is a hydrocarbon group having a carbon number of 1 to 8.

The foregoing $R^2$ is a substituted hydrocarbon group or an unsubstituted hydrocarbon group. The preferable $R^2$ is a hydrocarbon group having a carbon number of 1 to 8. All of $R^2$ may be identical to each other, and may differ from each other.

The foregoing $R^3$ is a substituted hydrocarbon group, a substituted heterocyclic group, an unsubstituted hydrocarbon group, or an unsubstituted heterocyclic group. The preferable $R^3$ is a hydrocarbon group having a carbon number of 1 to 8.

The foregoing $R^4$ is an electron-withdrawing group. The preferable electron-withdrawing group is, for example, an alkoxycarbonyl group, an acyl group, an arylsulfonyl group, or an alkylsulfonyl group.

The foregoing fluorenyl group is a ring-substituted fluorenyl group or a ring-unsubstituted fluorenyl group Next, the Mannich-type reaction using the glycine Schiff base is described (Scheme 2-1-12).

Scheme 2-1-12. Mannich-type reaction using glycine Schiff base derived from fluorenone

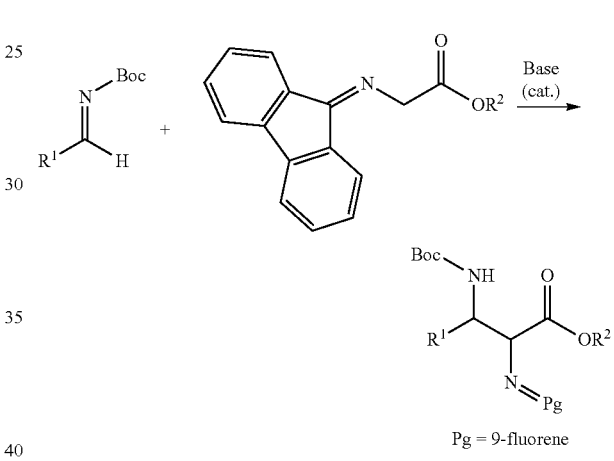

Further, the Mannich-type reaction using the glycine Schiff base phosphorus analogues (α-anion equivalent) is described (Scheme 2-1-13).

Scheme 2-1-13. Mannich-type reaction using glycine Schiff base phosphorous analogue derived from fluorenone

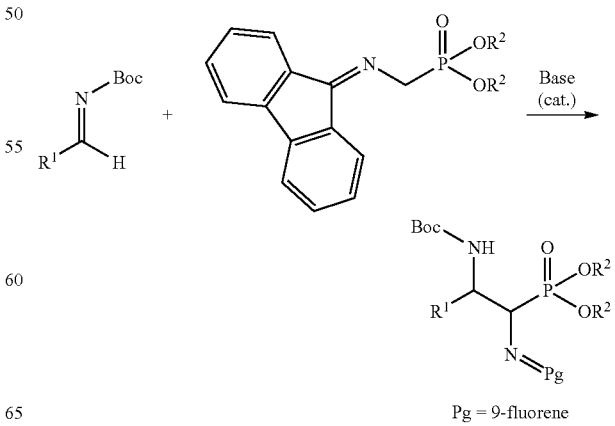

[Development of the Mannich-type reaction using the glycine Schiff base]

(1) Investigation of the Substrate Synthesis

O'Donnel et al. reported the glycine Schiff base derived from benzophenone (the glycine Schiff base using glycine ester hydrochloride and the benzophenone imine) (Scheme 2-2-1).

Scheme 2-2-1.

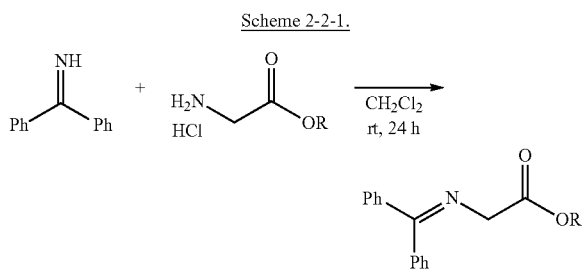

Thereupon, likewise, the fluorenone imine and the glycine ester hydrochloride were stirred for 24 hours in order to recrystallize them in a methylene chloride. The target product, however, was not obtained. Additionally, a dimer of the target product was obtained (Figure 2-2-1).

Thereupon, the various conditions were changed for investigation. However, only the dimer was obtained. The after-treatment (the cleaning by the base, the acid, a buffer solution, etc.) was conducted; however no target product was obtained.

FIG. 2-2-1. Proposed structure of Dimer

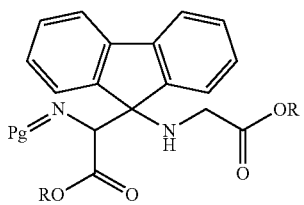

Pg = 9-fluorene

The reaction time was also investigated. For example, when the reaction stopped after one hour elapsed, the target product was obtained. No dimer thereof was obtained. When the reaction stopped after five hours elapsed, the target product was obtained at an excellent yield (Scheme 2-2-2).

Also in the synthesis of this substrate, the filtering/cleaning were conducted after the reaction, similarly to the case of the glycine Schiff base derived from benzophenone. And, the recrystallization was conducted. With this, the target product was obtained.

Scheme 2-2-2.

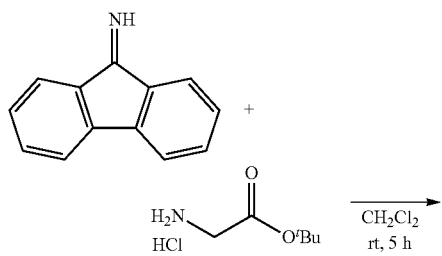

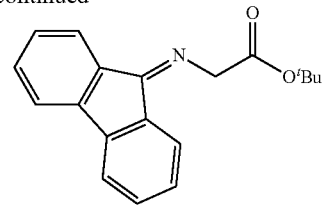

66% (recrystallized)

Methyl ester and tert-butyl ester were synthesized. And, they are employed for the following investigation (Figure 2-2-2).

FIG. 2-2-2. Structure of glycine Schiff bases

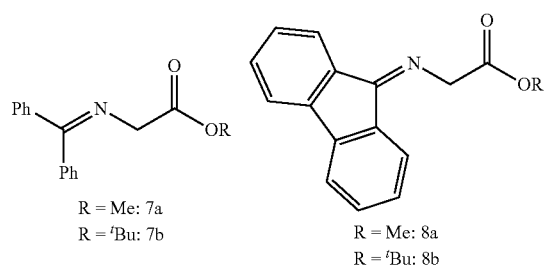

R = Me: 7a
R = $^t$Bu: 7b

R = Me: 8a
R = $^t$Bu: 8b (2) Investigation of the Reaction Conditions

A comparison between the reactivity of the Schiff base derived from benzophenone (7a) and that of the Schiff base derived from fluorenone (8a) was conducted in the presence of triethylamine by using N-tosylimine (Scheme 2-2-3).

When the Schiff base derived from fluorenone (8a) was used, the reaction progressed quantitatively. When the Schiff base derived from benzophenone (7a) was used, the yield was low.

It was known from the above result that the Schiff base derived from fluorenone was abundant in the reactivity. It was suggested that the rate-determining stage of the reaction was a stage of generating the nucleophiles by the deprotonation.

Scheme 2-2-3. Comparison of reactivity

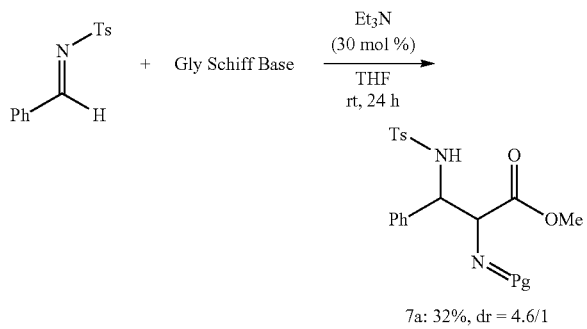

7a: 32%, dr = 4.6/1
8a: quant, dr = 2.3/1

When the N-tosylimine was used, the diastereoselectivity was low. Thereupon, the diastereoselectivity was greatly improved as a result of using the imine having the Boc group (Table 2-2-1, entry 1). Continuously, the organic bases were screened (entries 2 to 6). When DBU was used, the reaction time was shortened; however, a decline in the diastereoselectivity was confirmed (entry 3). When the reaction temperature was −20° C., no improvement was confirmed (entry 4). When tetramethylguanidine was used, both of the reaction time and the selectivity were excellent (entry 5). When the reaction temperature was lowered, an improvement in the selectivity was recognized (entry 6). When the substrate (8b) having a bulky tert-butyl ester group was used, the obtained target product (adduct) exhibits the high diastereoselectivity (entry 7). When the substrate derived from benzophenone (7b) was used under this condition, the reaction did not progressed (entry 8). LiOPMP is also effective as a catalyst, and the obtained target product exhibited the high yield (short time)/high diastereoselectivity (entry 9). Additionally, with an X-ray crystal structure analysis, it was known that the syn-type product was a main product in the case of using any of 8a and 8b (FIG. 2-2-3).

TABLE 2-2-1

Investigation of catalyst and conditions

| entry | Gly | base | T (° C.) | t (h) | yield (%) | syn/anti |
|---|---|---|---|---|---|---|
| 1 | 8a | Et$_3$N | rt | 36 | quant | 13.9/1 |
| 2 | 8a | $^i$Pr$_2$NEt | rt | 36 | 83 | 4.6/1 |
| 3 | 8a | DBU | rt | 0.5 | quant | 1.8/1 |
| 4 | 8a | DBU | −20 | 0.5 | quant | 2.1/1 |
| 5 | 8a | Guanidine[a] | rt | 0.5 | quant | 4.9/1 |
| 6 | 8a | Guanidine[a] | −20 | 0.5 | 72 | 9.2/1 |
| 7 | 8b | Guanidine[a] | −20 | 1 | 98 | >50/1 |
| 8 | 7b | Guanidine[a] | −20 | 16 | trace | — |
| 9 | 8a | LiOPMP[b] | −20 | 0.5 | quant | >99/1 |

[a]1,1,3,3-Tetramethylguanidine.
[b]Lithium p-methoxyphenoxide.

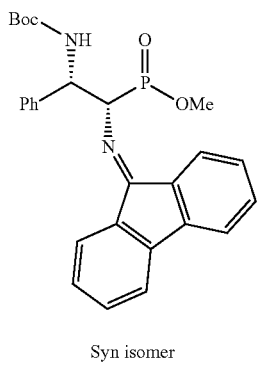

Syn isomer

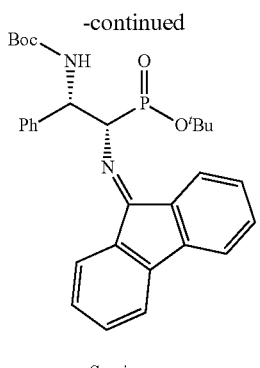

Syn isomer

Thereupon, the substrate generality was investigated in the case of using the tetramethylguanidine as a catalyst (Table 2-2-2). When the aromatic imine was used, the obtained target product exhibited the high yield/high diastereoselectivity (entries 1 to 4). When the imine derived from the aliphatic aldehyde was used, the adduct was obtained at an excellent yield. However, the diastereoselectivity declined greatly (entry 5).

TABLE 2-2-2

Substrate scope

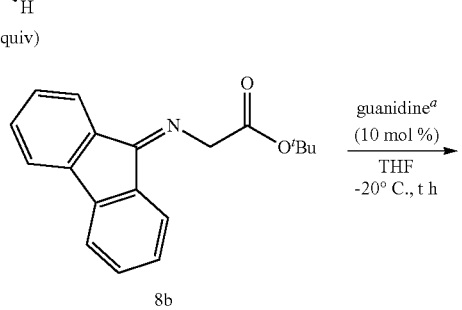

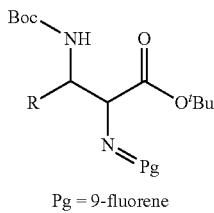

Pg = 9-fluorene

| entry | R | t (h) | yield (%) | syn/anti |
|---|---|---|---|---|
| 1 | Ph | 1 | 98 | >50/1 |
| 2 | p-MeOC$_6$H$_4$ | 16 | 91 | >50/1 |
| 3 | p-FC$_6$H$_4$ | 16 | 96 | 13.7/1 |
| 4 | 2-Furyl | 1 | 99 | 28.4/1 |
| 5[b] | Ph(CH$_2$)$_2$ | 16 | 84 | 4.0/1 |

[a]1,1,3,3-Tetramethylguanidine.
[b]2.0 equiv of imine.

When the imine derived from the alphatic aldehyde was used, the diastereoselectivity was in a middle level. Thereupon, in the case of using the substrate (8a) having the methylester, the LiOPMP, which afforded the excellent result, was used (Table 2-2-3). The reaction progressed smoothly. And, the obtained adduct exhibited the excellent diastereoselectivity.

TABLE 2-2-3

Mannich-type reactions using imine derived from aliphatic aldehyde

[Reaction scheme: N-Boc imine (R-CH=N-Boc, 2.0 equiv) + fluorenone-derived glycine methyl ester (8a) with LiOPMP$^a$ (2 mol %), THF, −20° C., 0.5 h, giving Boc-NH-CHR-CH(N=Pg)-C(O)OMe, Pg = 9-fluorene]

| entry | R | yield (%) | syn/anti |
|---|---|---|---|
| 1 | Ph(CH$_2$)$_2$ | 98 | 9.1/1 |
| 2 | Cyclohexyl | quant | 11.9/1 |

$^a$Lithium p-methoxyphenoxide.

(3) Application to the Asymmetric Reaction

The excellent result was obtained when the tetramethylguanidine was used. Thereupon, the development into the asymmetric reaction was conducted by using chiral guanidine.

The reaction using the chiral guanidine (the Michael reaction using the glycine Schiff base derived from benzophenone and the acrylate ester) was reported by Ishikawa et al. (Scheme 2-2-4). This reaction allows the enolate to be efficiently formed by a hydroxyl group introduced by the chiral guanidine (9). And, the obtained Michael adduct exhibited the high enantioselectivity. The deprotonation of the glycine Schiff base is slow. For this, it is necessary to use an excessive amount of the substrate. Thereupon, it was thought that using the glycine Schiff base derived from fluorenone, which was more easily deprotonated, enabled these problems to be alleviated.

Scheme 2-2-4. Asymmetric reaction catalyed chiral guanidine derivative

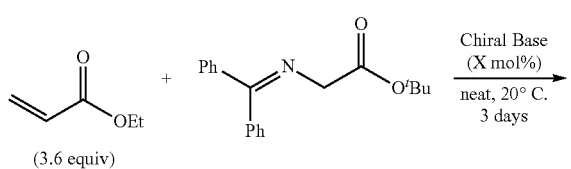

[Reaction scheme: ethyl acrylate (3.6 equiv) + Ph$_2$C=N-CH$_2$-C(O)O$^t$Bu with Chiral Base (X mol%), neat, 20° C., 3 days]

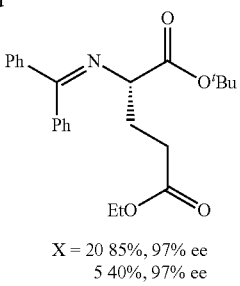

X = 20 85%, 97% ee
5 40%, 97% ee

[Chiral Base 9 structure]

Ishikawa, T. et. al.

The reaction conditions were investigated with N-Boc imine 8a derived from benzaldehyde defined as a model substrate (Table 2-2-4). The reaction progressed smoothly when THF was used as a solvent. However, the enantioselectivity was hardly recognized (entry 1). When the toluene (non-polar solvent) was used, the enantioselectivity was greatly improved (entry 2). Thereupon, the toluene was used as a solvent, and the reaction temperature was investigated. With the reaction at −45° C., a decline in the diastereoselectivity was confirmed. However, the obtained adduct exhibited the high enantioselectivity (entry 3). With the reaction at low temperature, a remarkable decline in the yield was confirmed. The diastereoselectivity furthermore declined (entry 4). When methylene chloride was used, the enantioselectivity was reversed (entry 5).

TABLE 2-2-4

Asymmetric Mannich-type reactions

[Reaction scheme: Ph-CH=N-Boc (1.2 equiv) + 8a (fluorenone glycine methyl ester) with chiral base 9 (10 mol %), Solvent, T° C., 16 h, X M]

TABLE 2-2-4-continued

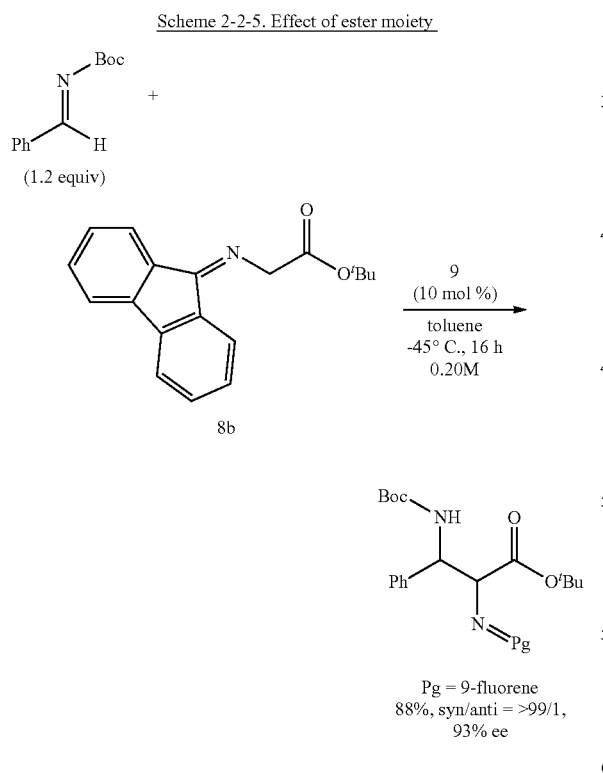

Pg = 9-fluorene

| entry | solvent | T | X | yield(%) | syn/anti | ee % (syn/anti) |
|---|---|---|---|---|---|---|
| 1 | THF | −20 | 0.07 | quant | 18.9/1 | 10/26 |
| 2 | Toluene | −20 | 0.07 | quant | 8.1/1 | 80/61 |
| 3 | Toluene | −45 | 0.20 | quant | 5.9/1 | 92/82 |
| 4 | Toluene | −78 | 0.20 | <28 | 1.8/1 | 91/85 |
| 5 | $CH_2Cl_2$ | −45 | 0.20 | quant | 20.0/1 | −57/−81 |

The reaction using the substrate (8b) having the tert-butyl ester group was conducted (Scheme 2-2-5). The reaction progressed smoothly, and the obtained target pruduct exhibited the high yield/high diastereoselectivity/high enantioselectivity.

Scheme 2-2-5. Effect of ester moiety

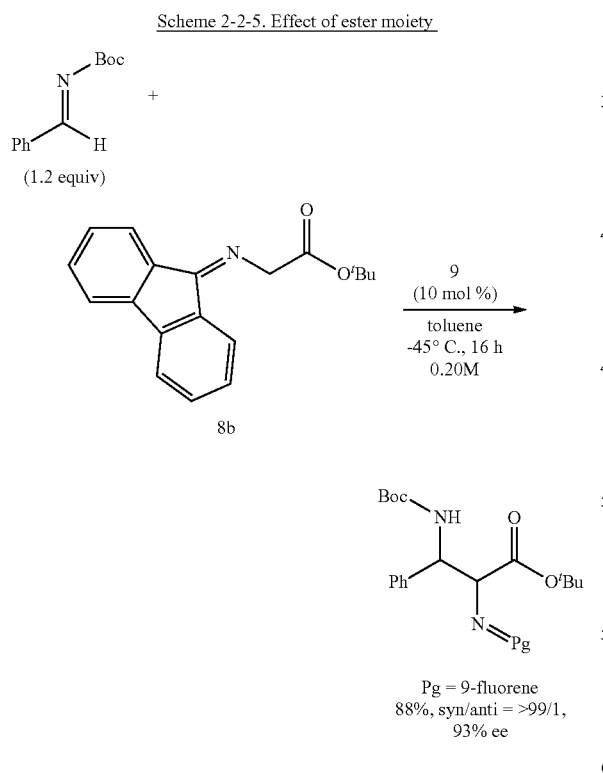

Pg = 9-fluorene
88%, syn/anti = >99/1,
93% ee

Likewise, the reaction was conducted under the identical conditions by using the substrate (8b) derived from benzophenone. However, the target product was hardly obtained even though the reaction temperature was raised to 80° C. (Scheme 2-2-6).

Scheme 2-2-6. Glycine Schiff base derived from benzophenone

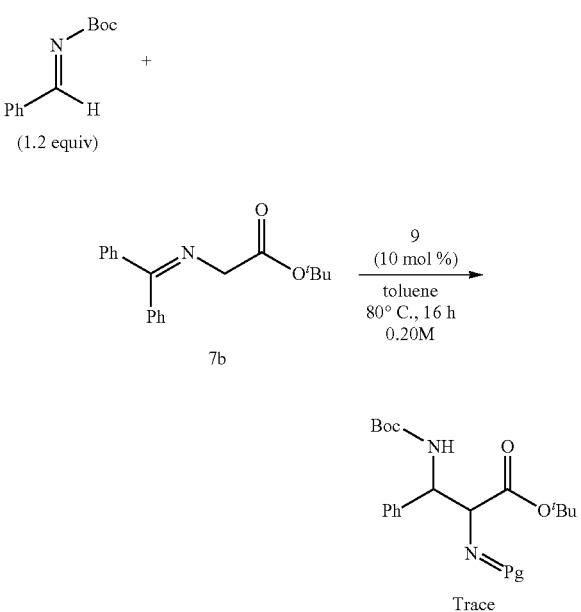

Trace

[Development of the Mannich-Type Reaction Using the Glycine Schiff Base Phosphonic Acid]

The α, β-diamino phosphonic acid is a medicinally/chemically interesting product. As a technique of synthesizing this α, β-diamino phosphonic acid, similarly to the case of the glycine alkyl ester, the Mannich-type reaction between the α-anion equivalent of the glycine Schiff base phosphonic acid analogues ($Gly^p$ Schiff base) and the imine (imine equivalent) was thinkable (Scheme 2-3-1).

Scheme 2-3-1.
Mannich-type reactions of glycine Schiff base phosphorus analogues

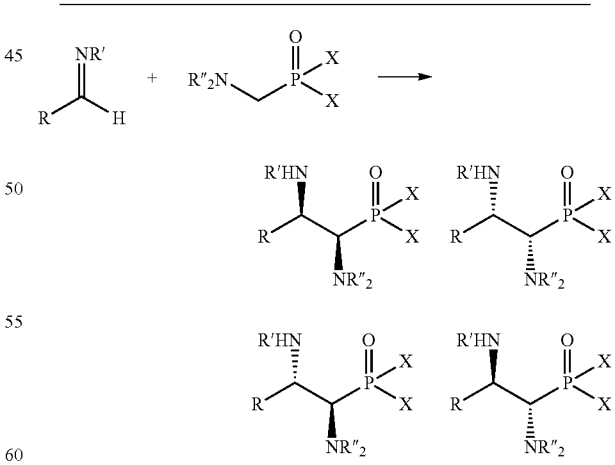

However, the acidity of the α-position hydrogen is low as compared with that of the glycine Schiff base. For this, the number of the reaction examples is very few (Figure 2-3-1). Hereinafter, its reaction example is shown.

FIG. 2-3-1. pKa values of glycine Schiff base (in DMSO) [8), 17)]

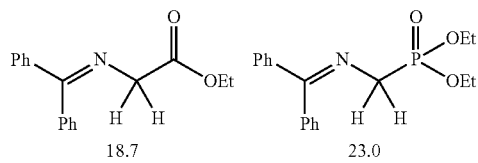

Genet et al. reported the alkylation using the phase transfer catalyst of the liquid (Scheme 2-3-2). They reported that when TBAB was used as a solvent, the yield was in a middle level, and potassium carbonate was not satisfactory as a base.

Scheme 2-3-2.

Genet, J. P. et al. (1990)

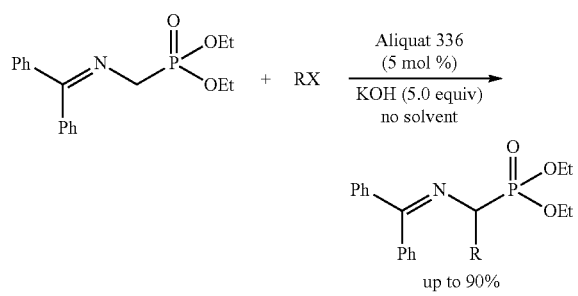

Kim et al. reported the Michael reaction using the phase transfer catalyst (Scheme 2-3-3-above). The Michael adduct was obtained at a high yield for various acrylate esters. Jaszay et al. reported the asymmetric Michael reaction (Scheme 2-3-3-down). However, one equivalent of the asymmetric sources was required, and the room for further improvement was left hereto in terms of the enantioselectivity. In any of these examples, one equivalent of the bases or more was used. And, the development of the high-reactivity substrate was desired.

Scheme 2-3-3.

Kim, D. Y. et al. (1990)

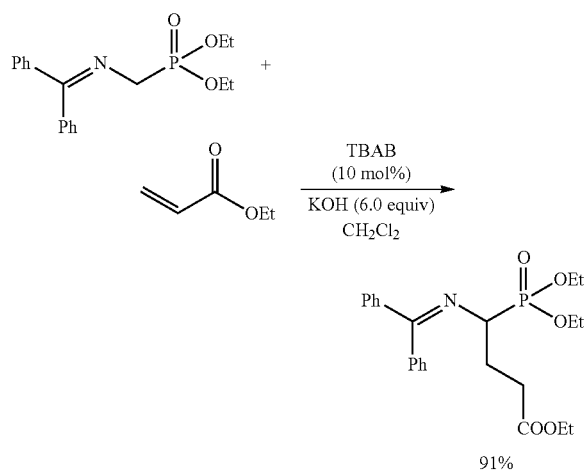

Jászay, Z. M.. et al. (2005)

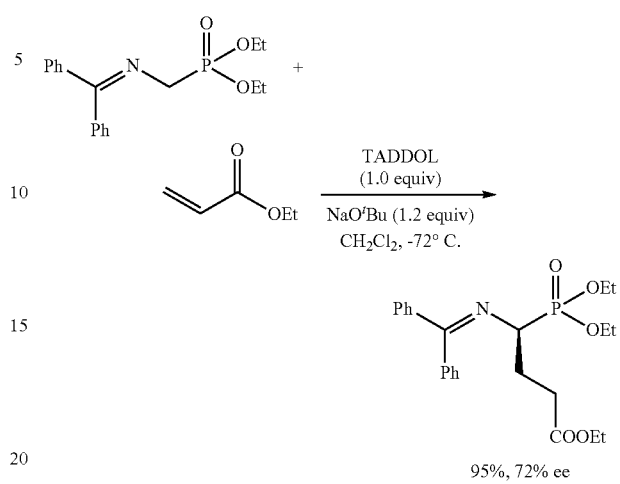

Gajda et al. reported the reaction affording the α, β-diamino phosphonic acid (the Mannich-type reaction using isothiocyanate phosphonic acid ester (Scheme 2-3-4). One equivalent of the bases or more was required also in this case. Yet, the above reaction requires use of mercury at the time of converting the product. For this, it is not satisfactory. When the imine derived from the aliphatic aldehyde was used, the yield was in a middle level. And, the room for further improvement was left hereto also in terms of the substrate generality.

Scheme 2-3-4.

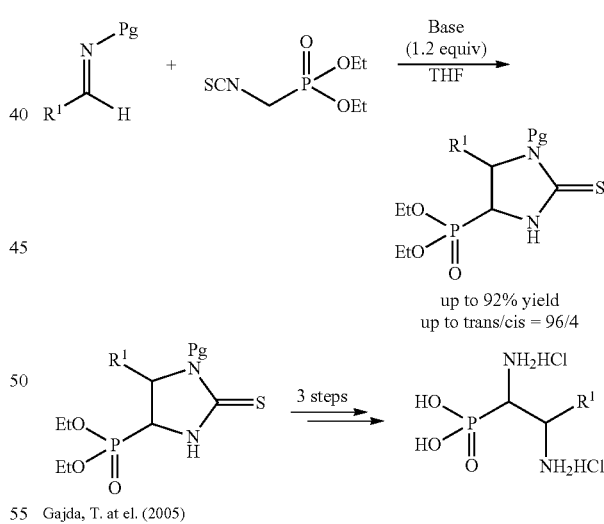

Gajda, T. at el. (2005)

(1) Investigation of the Reaction Conditions

The reactions using various bases were conducted with N-tosylimine defined as an electrophile (Table 2-3-1). While DBU, KO$^t$Bu, etc. each having the high deprotonation ability as an organic base were used, the reaction did not progress at all (entries 1 to 5). In the case of using the N-Boc imine that gave the excellent result in the glycine Schiff base, a small amount of the adduct was obtained when triethylamine was used (entry 6). When DBU and LiOPMP were used, the adduct was obtained at a high yield (entries 7 and 8).

TABLE 2-3-1

Ph−CH=N−R + [fluorenylidene-N-CH2-P(=O)(OEt)2] (10a) →(Base, solvent, rt, 24 h)→ Ph−CH(NHR)−CH(P(=O)(OEt)2)−N=Pg Pg = 9-fluorene

| entry | R | base (mol %) | solvent | yield (%) | dr |
|---|---|---|---|---|---|
| 1 | Ts | Et$_3$N (10) | THF | N.R. | — |
| 2 | Ts | CuOTf + Et$_3$N (10) | THF | N.R. | — |
| 3 | Ts | DBU (10) | THF | N.R. | — |
| 4 | Ts | DBU (30) | DMF | N.R. | — |
| 5 | Ts | KO$^t$Bu (30) | DMF | N.R. | — |
| 6 | Boc | NEt$_3$ (10) | DMF | low | N.D. |
| 7 | Boc | DBU (10) | DMF | 97 | 2.21/1 |
| 8 | Boc | LiOPMP (10) | THF | quant | 6.41/1 |

When LiOPMP was used, the adduct exhibiting the excellent diastereoselectivity was obtained for a short time. Thereupon, the comparison of the reactivity with substrates (11) and (12) derived from benzophenone, and the investigation of the temperature conditions were conducted (Table 2-3-2). In a case of using 10a, the reaction finished quickly, and the adduct was obtained quantitatively (entry 1). In a case of using 11, while the reaction time was prolonged, the yield was in a middle level (entry 2). In a case of using 12, while the reactivity was relatively high (entry 3), the adduct was hardly obtained at −78° C. (entry 6). In a case of using 10a, the reaction progressed smoothly even at −78° C. (entry 5). The target product was obtained quantitatively (entry 7) even though the amount of the catalyst was reduced to 2 mol %. It was known from the above result that the substrate (10a) derived from fluorenone was high in the acidity of the α-position hydrogen and was easily deprotonated as compared with the substrate (12) derived from benzophenone having the strong electron-withdrawing group such as CF$_3$.

TABLE 2-3-2

Comparison of reactivity

Ph−CH=N−Boc + Gly$^P$ Schiff Base →(LiOPMP (10 mol %), THF, T° C., t min)→

TABLE 2-3-2-continued

Ph−CH(NHBoc)−CH(P(=O)(OEt)2)−N=Pg

Pg = 9-fluorene

| entry | Gly$^P$ | T (° C.) | t (min) | yield (%) | dr |
|---|---|---|---|---|---|
| 1 | 10a | 0 | 10 | quant | 11.4/1 |
| 2 | 11 | 0 | 960 | 65 | N.D. |
| 3 | 12 | 0 | 10 | 95 | 15.0/1 |
| 4 | 10a | −20 | 10 | 98 | 15.1/1 |
| 5 | 10a | −78 | 10 | 82 | 23.0/1 |
| 6 | 12 | −78 | 10 | Trace | N.D |
| 7[a] | 10a | −78 | 960 | quant | 18.4/1 |

[a] Catalyst loading was 2 mol %.
N.D. = not determined

10a: fluorenylidene-N-CH2-P(=O)(OEt)2

Ar−C(Ar)=N−CH2−P(=O)(OEt)2

11: Ar = Ph
12: Ar = 4-CF$_3$C$_6$H$_4$

Next, the catalysts were screened with a time (Xh) required until a conversion rate reaches 100% and the diastereoselectivity defined as a marker, respectively (Table 2-3-3). A large change in the selectivity by a counter anion of a lithium salt was not recognized (entries 1 and 2). When NaO$^t$Bu and the phase transfer catalyst were used, the diastereoselectivity was improved (entries 3 and 5). When various alkaline earth metals were used, the reaction progressed smoothly. However, the diastereoselectivity was low (entries 6 to 9). When Sc(O$^i$Pr)$_3$ and Zn(O$^t$Bu)$_2$ were used, the satisfactory result was not obtained (entries 10 and 11).

TABLE 2-3-3

Screening of bases

Ph−CH=N−Boc + [fluorenylidene-N-CH2-P(=O)(OEt)2] →(Base (10 mol %), THF, 0° C., time for 100% conversion (X h))→

TABLE 2-3-3-continued

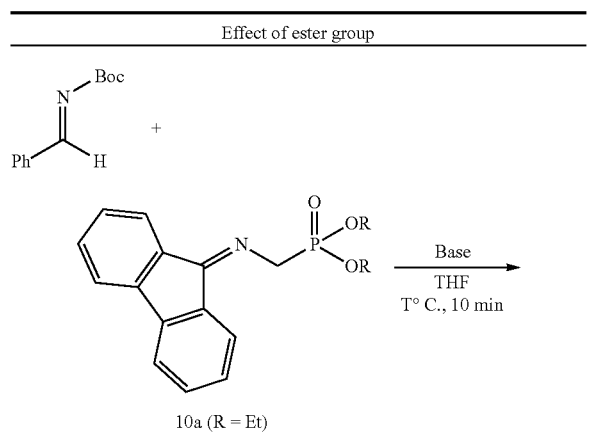

Pg = 9-fluorene

| entry | Base | X (h) | dr |
|---|---|---|---|
| 1 | LiOPMP | <0.1 | 11.4/1 |
| 2 | LiO$^t$Bu | <0.1 | 10.2/1 |
| 3 | NaO$^t$Bu | <0.1 | 12.5/1 |
| 4 | KO$^t$Bu | <0.1 | 7.0/1 |
| 5 | TBAB + KOHaq | <0.1 | 12.0/1 |
| 6 | Mg(O$^t$Bu)$_2$ | >12[b] | 1.1/1 |
| 7 | Ca(O$^i$Pr)$_2$ | 1.0 | 3.6/1 |
| 8 | Sr(O$^i$Pr)$_2$ | <0.1 | 3.1/1 |
| 9 | Ba(O$^t$Bu)$_2$ | <0.1 | 3.5/1 |
| 10 | Sc(O$^i$Pr)$_3$ | >12[b] | 2.3/1 |
| 11 | Zn(O$^t$Bu)$_2$ | —[c] | — |

[a]Reaction was conducted in liq-liq bi-phase system; toluene (0.10 M), 50% KOHaq, TBAB (10 mol %), 0° C., 10 min.
[b]Reaction did not complete even in 12 h (Isolated yield: 64% for Mg, 68% for Sc).
[c]Trace (even at rt for 12 h).

So as to enhance the selectivity, the investigation was conducted by using the substrate (10b) having the bulky isopropylester (Table 2-3-4). When LiOPMP was used, the diastereoselectivity was improved remarkably (entry 4). When the reaction was conducted by using NaO$^t$Bu, at 0° C., the obtained adduct exhibited the high diastereoselectivity (entry 5). At −20° C., the yield declined slightly (entry 6). The X-ray crystal structure analysis demonstrated that the syn-type product was a main product even with the reaction using 10b (FIG. 2-3-3).

TABLE 2-3-4

Effect of ester group

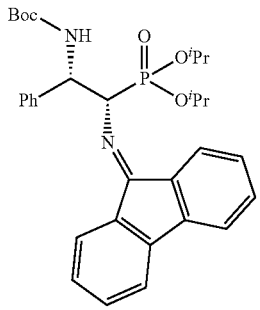

| entry | R | base (mol %) | T (° C.) | Yield (%) | syn/anti |
|---|---|---|---|---|---|
| 1 | Et | LiOPMP (10) | 0 | quant | 11.4/1 |
| 2 | Et | LiOPMP(10) | −78 | 82 | 23.0/1 |
| 3 | Et | NaO$^t$Bu (10) | 0 | 94 | 12.5/1 |
| 4 | $^i$Pr | LiOPMP (10) | 0 | quant | 27.6/1 |
| 5 | $^i$Pr | NaO$^t$Bu (2) | 0 | 95 | >50/1 |
| 6 | $^i$Pr | NaO$^t$Bu (2) | −20 | 86 | >50/1 |

Syn isomer

The substrate generality was investigated because the optimum conditions were obtained (Table 2-3-5). When the aromatic imine was used, the reaction progressed smoothly. And, the obtained target product showed the high yield/high diastereoselectivity. In the imines derived from the aliphatic aldehyde, the target product was obtained at an excellent yield when two equivalents of the imines as an electrophile were used.

TABLE 2-3-5

Substrate Scope

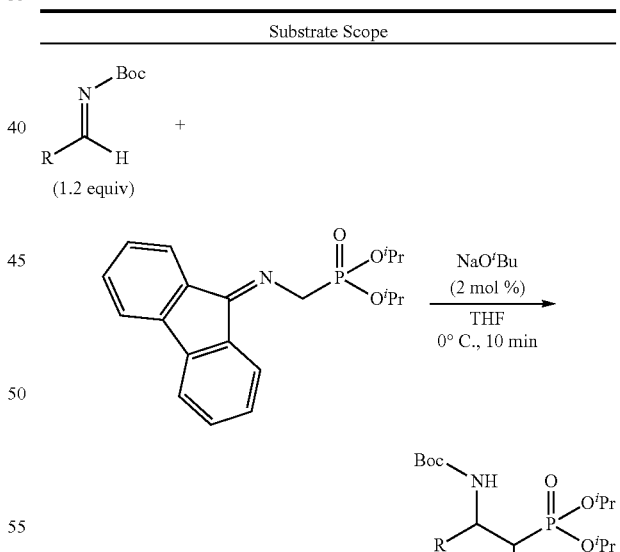

Pg = 9-fluorene

| entry | R | yield (%) | syn/anti |
|---|---|---|---|
| 1 | Ph | 95 | >50/1 |
| 2 | p-MeOC$_6$H$_4$ | quant | 12.9/1 |
| 3 | p-FC$_6$H$_4$ | 97 | 27.4/1 |
| 4 | m-MeC$_6$H$_4$ | 96 | 21.7/1 |
| 5 | o-MeC$_6$H$_4$ | 99 | >99/1 |

TABLE 2-3-5-continued

| | | | |
|---|---|---|---|
| 6[a] | m-vinylC$_6$H$_4$ | quant | >50/1 |
| 7 | 2-Furyl | quant | 23.4/1 |
| 8[a] | 2-Thienyl | quant | 32.9/1 |
| 9[b] | Ph(CH$_2$)$_2$ | 88 | >99/1 |
| 10[b] | Cyclohexyl | quant | >99/1 |

[a]16 h.
[b]2.0 equiv of imine.

(2) Investigation of the Deprotection

So as to show usefulness of the product, the investigation for removing the fluorenyl group was conducted. The deprotection was easily conducted under a mild acidic condition. For example, the deprotected product was obtained as a hydrochloride (Scheme 2-3-4). Additionally, the Boc group was not removed under this condition.

Scheme 2-3-4.

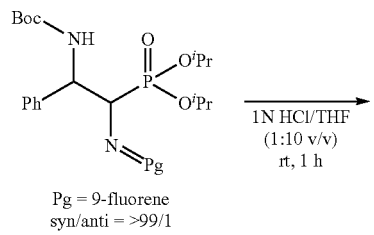

Pg = 9-fluorene
syn/anti = >99/1

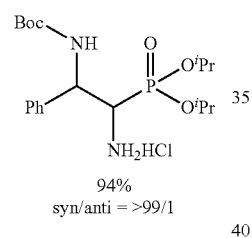

94%
syn/anti = >99/1

Hereinafter, specific examples will be explained furthermore.

[A Manufacturing Method of the Diamino Acid and the Diamino Phosphonic Acid Derivatives]

(1) Synthesis of the Diamino Acid Ester

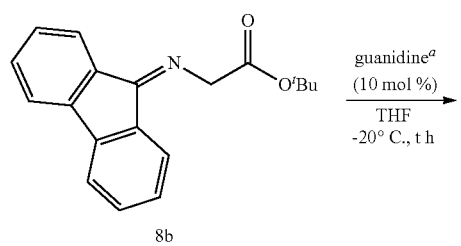 [SMILES: CC(C)(C)OC(=O)CN=C1c2ccccc2-c2ccccc21]

8b

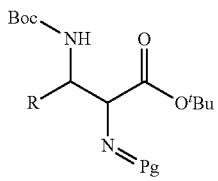

Pg = 9-fluorene

| entry | R | t (h) | yield (%) | syn/anti |
|---|---|---|---|---|
| 1 | Ph | 1 | 98 | >50/1 |
| 2 | p-MeOC$_6$H$_4$ | 16 | 91 | >50/1 |
| 3 | p-FC$_6$H$_4$ | 16 | 96 | 13.7/1 |
| 4 | 2-Furyl | 1 | 99 | 28.4/1 |
| 5[b] | Ph(CH$_2$)$_2$ | 16 | 84 | 4.0/1 |

[a]1,1,3,3-Tetramethylguanidine.
[b]2.0 equiv of imine.

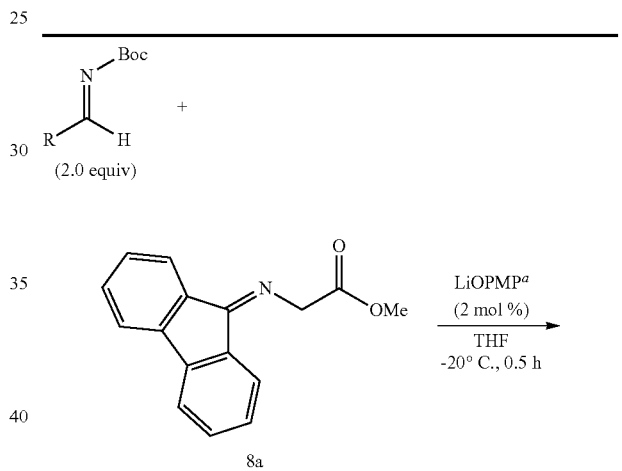

8a

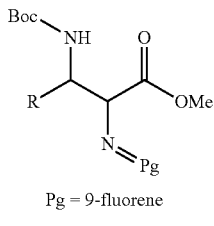

Pg = 9-fluorene

| entry | R | yield (%) | syn/anti |
|---|---|---|---|
| 1 | Ph(CH$_2$)$_2$ | 98 | 9.1/1 |
| 2 | Cyclohexyl | quant | 11.9/1 |

[a]Lithium p-methoxyphenoxide.

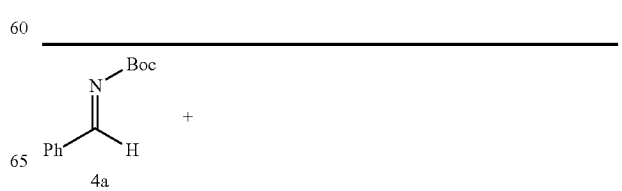

4a

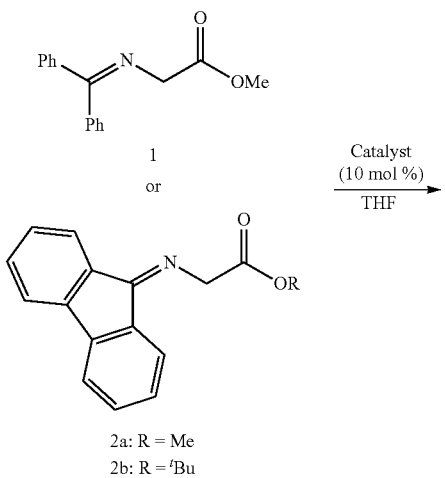

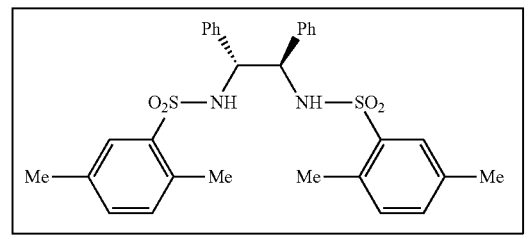

[A Manipulation of the Asymmetric Mannich-Type Reaction Between the Fluoren Glycine ester and the Boc imine]

The depressurized, dried, and heated reactor with a capacity of 10 mL was argon-substituted. This reactor was carried into a glove-box. And, ligand (0.018 mmol), molecular sieves 4A (50 mg), and Ca(O$^i$Pr)$_2$ (0.015 mmol) were sequentially measured. After the reactor was taken out from the glove-box, the toluene (0.15 mL) was poured with a gastight syringe. Thereafter, it was stirred for two hours at room temperature. With this, the catalyst was prepared. After preparing the catalyst, a toluene solution (0.2 mL) of a fluoren protective tert-butylglycine ester (0.15 mmol) and a toluene solution (0.3 mL) of the Boc imine are sequentially added at 40° C. with the gastight syringe. And, after the finishing of the reaction was confirmed with TLC (developing solvent: hexane/acetone=4/1), a saturated ammonium chloride aqueous solution (5 mL) was added, and the reaction was stopped. Thereafter, the extraction was conducted four times with methylene chloride (10 mL). It was dried over anhydrous sodium sulfate. After filtering, concentration under reduced pressure was conducted. The crude product obtained in such a manner was refined with a silica gel thin-layer chromatography, and the target product (α, β-diamino acid derivatives) was obtained.

The yield was 78%. The diastereoselectivity was syn/anti=1.5/1. With the enantioselectivity, the syn-type product was obtained at rate of 71%. Additionally, the diastereoselectivity and the enantioselectivity were determined with HLPC.

$^1$H NMR (CDCl$_3$): δ: 1.45 (s, 9H), 1.49 (s, 9H), 5.20 (s, 1H), 5.64 (d, J=7.9 Hz, 1H), 6.37 (d, J=7.9 Hz, 1H), 7.13-7.58 (m, 12H), 7.89 (d, J=7.4 Hz, 1H).

$^{13}$C NMR (CDCl$_3$): δ: 27.9, 28.4, 56.7, 56.8, 68.9, 79.3, 82.8, 119.3, 120.5, 123.1, 126.5, 127.0, 127.1, 127.8, 128.2, 128.4, 131.4, 131.7, 131.8, 141.2, 144.0, 155.3, 166.8, 168.3.

HPLC Daicel Chiralpak Hexane AD-H, Hexane/$^1$PrOH=4/1, Flow rate=1.00 mL/min,

Detection wavelength=254 nm: syn isomer: t$_R$=5.1 min (major), t$_R$=32.2 min (minor). anti isomer: t$_R$=6.7 min (major), t$_R$=11.3 min (minor).

(1-1) Synthesis of the Substrate

Boc-imine

It was synthesized in accordance with the foregoing Non-patent documents. The imine derived from the aliphatic aldehyde was also synthesized in accordance with the foregoing Non-patent documents. And, it was quickly used for the reactions.

| entry | Gly | catalyst | temp/° C. | time/h | yield/% | syn/anti |
|---|---|---|---|---|---|---|
| 1 | 1 | Guanidine[a] | −20 | 16 | trace | — |
| 2 | 2b | Guanidine | −20 | 1 | 98 | >99/1 |
| 3 | 2a | LiOPMP | −20 | 0.5 | quant | >99/1 |

[a]1,1,3,3-Tetramethylguanidine.

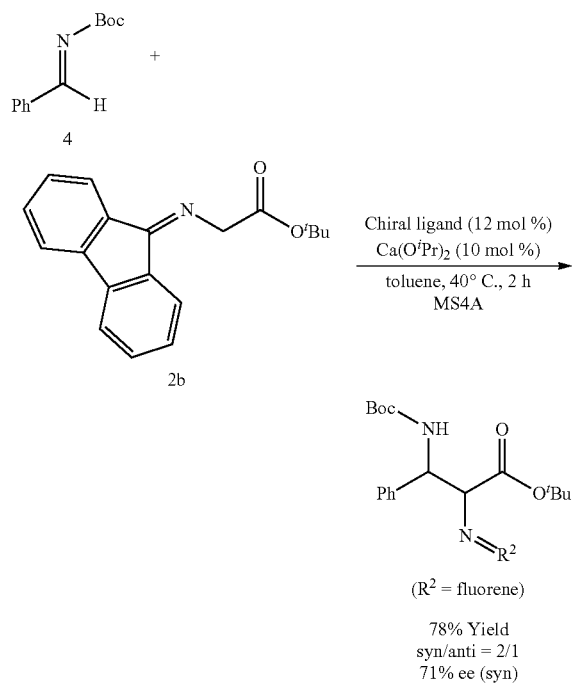

Fluoren-9-ylideneamine

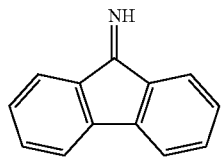 [SMILES: N=C1c2ccccc2-c2ccccc21]

The fluorenone (4.0 g, 22.2 mmol) was stirred in an autoclave of 110° C. for three days in an ammonia atmosphere (7 to 8 atm). After the reaction, it was allowed to dissolve in diethyl ether. And, hydrogen chloride was blown into it. It was stirred for one hour at room temperature. The obtained suspension was filtered, and the filtrate was cleaned with the diethyl ether. With this, fluorenone imine hydrochloride (3.4 g, 71%) was obtained. This hydrochloride was allowed to decompose with an ammonia aqueous solution. And, it was recrystallized by using the methylene chloride and hexane. And, Fluoren-9-ylideneamine (2.3 g, 58%) was obtained.

$^1$H NMR (CDCl$_3$): δ 7.31 (dt, J=1.1, 7.4 Hz, 2H), 7.44 (dt, J=1.1, 7.4 Hz, 2H), 7.54 (d, J=7.4 Hz, 2H), 7.73 (br d, J=7.4 Hz, 2H), 10.3 (s, 1H).

$^{13}$C NMR (CDCl$_3$): δ 120.1, 122.2, 128.20, 132.19, 132.20, 142.2, 173.2.

Glycine Schiff Base

The fluorenone imine (1.52 g, 8.48 mmol) and the glycine tert-butylester hydrochloride (1.42 g, 8.48 mmol) were stirred in the methylene chloride for five hours at room temperature. The reaction solution was filtered with celite, and the solvent was removed by the distillation under reduced pressure. The obtained residual was allowed to dissolve in the diethyl ether. And, it was filtered with the celite. The obtained ether solution was cleaned with water and a saturated sodium chloride aqueous solution. And, it was dried over sodium sulfate. After the filtering and the concentration under reduced pressure were conducted, the obtained crude product was refined with the diethyl ether/hexane (recrystallization). And, (Fluoren-9-ylideneamino)-acetic acid tert-butyl ester (1.18 g, 66%) was obtained.

(Fluoren-9-ylideneamino)-acetic acid tert-butyl ester

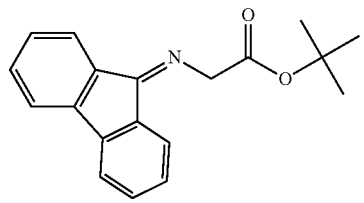 [SMILES: CC(C)(C)OC(=O)CN=C1c2ccccc2-c2ccccc21]

mp: 79-81° C.

IR(KBr): 2981, 1751, 1605, 1606, 1451, 1143 cm$^{-1}$.

$^1$H NMR (CDCl$_3$): δ 1.54 (s, 9H), 4.87 (s, 2H), 7.27-7.31 (m, 2H), 7.39-7.45 (m, 2H), 7.56 (d, J=7.4 Hz, 1H), 7.65 (d, J=7.4 Hz, 1H), 7.75 (d, J=7.9 Hz, 1H), 7.90 (d, J=7.4 Hz, 1H), $^{13}$C NMR (CDCl$_3$): δ 28.15, 28.16, 55.6, 81.6, 119.3, 120.5, 123.1, 127.3, 128.0, 128.4, 131.2, 131.7, 131.9, 141.1, 143.9, 165.5, 170.0.

ESI-HRMS m/z calcd for C$_{19}$H$_{19}$NO$_2$: 294.1494 [M+H]$^+$. found: 294.1475.

Anal. Calcd for C$_{19}$H$_{19}$NO$_2$: C, 77.79; H, 6.53; N, 4.77. found: C, 77.66; H, 6.64; N, 4.74.

Likewise, (Fluoren-9-ylideneamino)-acetic acid methyl ester was obtained.

(Fluoren-9-ylideneamino)-acetic acid methyl ester

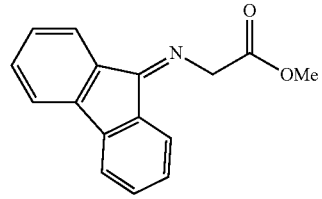 [SMILES: COC(=O)CN=C1c2ccccc2-c2ccccc21]

mp: 103-105° C.

IR(KBr): 3052, 2951, 1726, 1448, 1268, 1013 cm$^{-1}$.

$^1$H NMR (CDCl$_3$): δ 3.86 (s, 3H), 4.96 (s, 2H), 7.26-7.31 (m, 2H), 7.41 (t, J=7.6 Hz, 1H), 7.45 (t, J=7.6 Hz, 1H), 7.55 (d, J=7.6 Hz, 1H), 7.65 (d, J=7.6 Hz, 1H), 7.73 (d, J=7.6 Hz, 1H), 7.88 (d, J=7.6 Hz, 1H).

$^{13}$C NMR (CDCl$_3$): δ 52.3, 55.0, 119.4, 120.6, 123.1, 127.2, 128.1, 131.3, 131.7, 131.8, 137.9, 141.1, 143.9, 165.6, 171.0.

ESI-HRMS m/z calcd for C$_{16}$H$_{13}$NO$_2$: 252.1025 [M+H]$^+$. found: 252.1020.

Anal. Calcd for C$_6$H$_{13}$NO$_2$: C, 76.48; H, 5.21; N, 5.57. found: C, 76.29; H, 5.36; N, 5.39

1-2) A General Manipulation of Synthesizing the Diamino Acid Ester

A THF solution (0.40 mL) of the glycine Schiff base (58.7 mg, 0.2 mmol) was stirred at −20° C. A solution (0.1 mL) containing THF and tetramethylguanidine (tetramethylguanidine: THF=0.2 mmol: 1.0 mL), and a THF solution (0.50 mL) of the imine (49.3 mg, 0.24 mmol) were sequentially added. And, the stirring-up was conducted for one hour with the temperature kept at −20° C. Thereafter, a saturated ammonium chloride aqueous solution was added, and the reaction was stopped. Thereafter, the temperature was raised (to the room temperature). The extraction from the water phase was carried out with the methylene chloride three times. And, the organic phase was collected, and dried over anhydrous sodium sulfate. After the filtering and the concentration under reduced pressure, the obtained crude product was refined with the thin-layer silica gel chromatography (hexane/acetone=4/1). With this, the target product was obtained. The diastereomer ratio was determined with the HPLC analysis.

3-tert-Butoxycarbonylamino-2-(fluoren-9-ylideneamino)-3-phenyl-propionic acid methyl ester

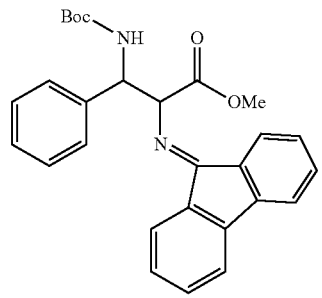 [SMILES: COC(=O)C(N=C1c2ccccc2-c2ccccc21)C(NC(=O)OC(C)(C)C)c1ccccc1]

mp: 57-59° C. IR(KBr): 3441, 2976, 1718, 1492, 1171 cm⁻¹. ¹H NMR (CDCl₃): δ 1.46 (s, 9H), 3.78 (s, 3H), 5.32 (s, 1H), 5.62 (d, J=7.6 Hz, 1H), 6.35 (d, J=6.2 Hz, 1H), 7.14-7.26 (m, 4H), 7.31-7.45 (m, 6H), 7.52 (d, J=7.6 Hz, 1H), 7.58 (d, J=7.6 Hz, 1H), 7.90 (d, J=7.6 Hz, 1H).
¹³C NMR (CDCl₃): δ 28.3, 28.37, 28.43, 52.7, 56.87, 56.90, 68.3, 79.6, 119.4, 120.6, 123.2, 126.5, 126.9, 127.3, 128.1, 128.3, 128.4, 128.4, 131.56, 131.61, 131.9, 138.0, 141.21, 141.23, 144.1, 155.4, 167.1, 170.2.
FAB-HRMS m/z calcd for $C_{28}H_{28}N_2O_4$: 457.2127 [M+H]⁺. found: 457.2146. A*nal*. C*alcd* for $C_{28}H_{28}N_2O_4$: C, 73.66; H, 6.18; N, 6.14. found: C, 73.54; H, 6.28; N, 6.05.
HPLC (Daicel Chiralcel AD-H, hexane/iPrOH=4/1, flow rate=1.00 mL/min)
syn isomer: $t_R$=5.5 min (minor), $t_R$=21.0 min (major). Anti isomer: $t_R$=8.6 min, $t_R$=12.7 min.

3-tert-Butoxycarbonylamino-2-(fluoren-9-ylidene-amino)-5-phenyl-pentanoic acid methyl ester

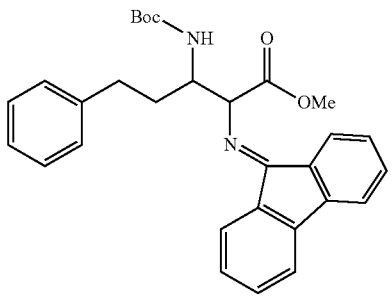 [SMILES: COC(=O)C(N=C1c2ccccc2-c2ccccc21)C(CCc1ccccc1)NC(=O)OC(C)(C)C]

mp: 52.5-55.5° C. IR(KBr): 3425, 2976, 1714, 1495, 1169 cm⁻¹. ¹H NMR (CDCl₃): δ 1.48 (s, 9H), 1.82-1.85 (m, 1H), 1.88-1.92 (m, 1H), 2.65-2.70 (m, 1H), 2.74-2.79 (m, 1H), 3.72 (s, 2H), 4.49-4.51 (m, 1H), 5.09 (s, 1H), 5.61 (d, J=10.3 Hz, 1H), 7.10-7.32 (m, 7H), 7.42 (t, J=7.6 Hz, 2H), 7.53 (d, J=7.6 Hz, 1H), 7.56 (d, J=7.6 Hz, 1H), 7.64 (d, J=7.6 Hz, 1H), 7.88 (d, J=6.9 Hz, 1H).
¹³C NMR (CDCl₃): δ 28.4, 32.6, 35.6, 52.5, 53.4, 66.7, 119.4, 120.6, 123.2, 125.8, 126.6, 128.2, 128.3, 128.4, 131.6, 131.9, 138.1, 141.6, 155.8, 170.6.
FAB-HRMS m/z calcd for $C_{30}H_{32}N_2O_4$: 485.2440 [M+H]⁺. found: 485.2438.

3-tert-Butoxycarbonylamino-3-cyclohexyl-2-(fluoren-9-ylideneamino)-propionic acid methyl eater

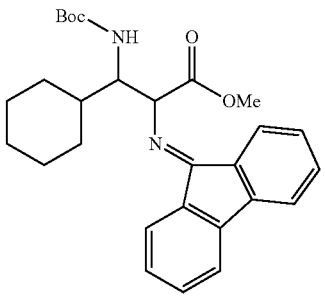 [SMILES: COC(=O)C(N=C1c2ccccc2-c2ccccc21)C(NC(=O)OC(C)(C)C)C1CCCCC1]

mp; 80-84° C. IR(KBr): 3426, 2927, 1730, 1429, 1171 cm⁻¹. ¹H NMR (CDCl₃): δ 1.08 (m, 6H), 1.46 (s, 9H), 1.57- 1.95 (m, 5H), 3.72 (s, 3H), 4.16 (t, J=10.0 Hz, 1H), 5.31 (s, 1H), 5.62 (d, J=10.3 Hz, 1H), 7.26 (d, J=7.2 Hz, 1H), 7.32 (d, J=7.2 Hz, 1H), 7.42-7.45 (m, 2H), 7.55-7.58 (m, 2H), 7.65 (d, J=7.6 Hz, 1H), 7.88 (d, J=6.9 Hz, 1H).
¹³C NMR (CDCl₃): δ 26.0, 26.2, 28.4, 29.66, 29.72, 40.2, 52.4, 58.1, 64.1, 79.0, 119.4, 120.6, 123.3, 126.5, 128.3, 128.4, 131.5, 131.6, 131.9, 138.1, 141.3, 144.1, 156.0, 166.6, 171.1.
FAB-HRMS m/z calcd for $C_{28}H_{34}N_2O_4$; 463.2597 [M+H]⁺. found: 463.2617.

3-tert-Butoxycarbonylamino-2-(fluoren-9-ylidene-amino)-3-phenyl-propionic acid tert-butyl ester

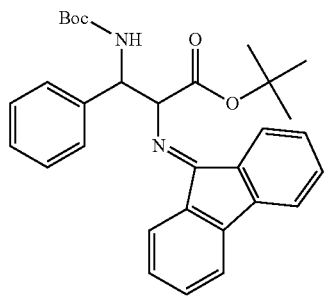 [SMILES: CC(C)(C)OC(=O)NC(c1ccccc1)C(N=C1c2ccccc2-c2ccccc21)C(=O)OC(C)(C)C]

mp: 187-188° C. IR(KBr): 3435, 2974, 1737, 1713, 1490, 1146 cm⁻¹. ¹H NMR (CDCl₃): δ 1.45 (s, 9H), 1.49 (s, 9H), 5.20 (s, 1H), 5.64 (d, J=7.9 Hz, 1H), 6.37 (d, J=7.9 Hz, 1H), 7.13-7.58 (m, 12H), 7.89 (d, J=7.4 Hz, 1H). ¹³C NMR (CDCl₃): δ 27.9, 28.4, 56.7, 56.8, 68.9, 79.3, 82.8, 119.3, 120.5, 123.1, 126.5, 127.0, 127.1, 127.8, 128.2, 128.4, 131.4, 131.7, 131.8, 138.1, 141.2, 144.0, 155.3, 166.8, 168.3.
ESI-HRMS m/z calcd for $C_{31}H_{34}N_2O_4$: 499.2597 [M+H]⁺. found: 499.2599. A*nal*. C*alcd* for $C_{31}H_{34}N_2O_4$: C, 74.67; H, 6.87; N, 5.62. found: C, 74.54; H, 7.01; N, 5.51.
HPLC (Daicel Chiralcel AD-H, hexane/iPrOH=4/1, flow rate=1.00 mL/min) syn isomer: $t_R$=5.1 min (minor), $t_R$=32.2 min (major). Anti isomer $t_R$=6.7 min, $t_R$=11.3 min.

3-tert-Butoxycarbonylamino-2-(fluoren-9-ylidene-amino)-3-(4-methoxy-phenyl)-propionic acid tert-butyl ester

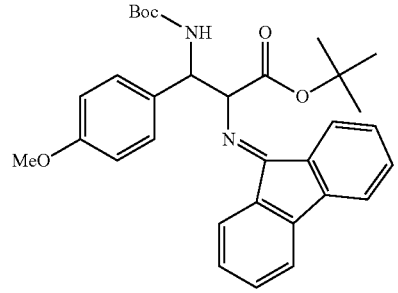 [SMILES: COc1ccc(C(NC(=O)OC(C)(C)C)C(N=C2c3ccccc3-c3ccccc32)C(=O)OC(C)(C)C)cc1]

mp: 174.5-181.5° C. IR(KBr): 3442, 2977, 1719, 1491, 1164 cm⁻¹. ¹H NMR (CDCl₃): δ 1.44 (s, 9H), 1.48 (s, 9H), 3.70 (s, 3H), 5.17 (s, 1H), 5.58 (d, J=6.9 Hz, 1H), 6.32 (d, J=6.2 Hz, 1H), 6.76 (d, J=8.9 Hz, 2H), 7.18 (t, J=7.6 Hz, 1H), 7.30-7.59 (m, 8H), 7.90 (d, J=7.6 Hz, 1H).

$^{13}$C NMR (CDCl$_3$): δ 22.7, 27.76, 27.80, 28.1, 28.4, 55.16, 55.23, 56.2, 69.1, 79.3, 82.7, 113.5, 113.6, 119.3, 120.5, 123.1, 126.6, 127.9, 128.0, 128.2, 128.4, 131.4, 131.8, 141.2, 144.0, 155.2, 158.7, 166.8, 168.4.

ESI-HRMS m/z calcd for C$_{32}$H$_{36}$N$_2$O$_5$: 529.2702 [M+H]$^+$. found: 529.2694.

3-tert-Butoxycarbonylamino-2-(fluoren-9-ylidene-amino)-3-(4-fluoro-phenyl)-propionic acid tert-butyl ester

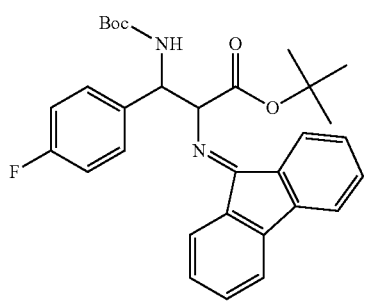 [SMILES: CC(C)(C)OC(=O)NC(c1ccc(F)cc1)C(N=C1c2ccccc2-c2ccccc21)C(=O)OC(C)(C)C]

mp: 155-159° C. IR(KBr): 3445, 2979, 1722, 1490, 1158 cm$^{-1}$. $^1$H NMR (CDCl$_3$): δ 1.45 (s, 9H), 1.48 (s, 9H), 5.16 (s, 1H), 5.60 (d, J=6.9 Hz, 1H), 6.34 (d, J=6.9 Hz, 1H), 6.92 (t, J=8.6 Hz, 2H), 7.17-7.60 (m, 9H), 7.88 (d, J=7.6 Hz, 1H).
$^{13}$C NMR (CDCl$_3$): δ 27.9, 28.2, 28.4, 56.2, 68.9, 79.5, 82.9, 115.0, 115.1, 119.4, 120.6, 123.0, 126.5, 127.9, 128.4, 128.6, 128.7, 131.5, 131.7, 131.9, 137.0, 138.0, 141.2, 144.1, 155.2, 161.2, 162.8, 167.0, 168.2.
ESI-HRMS m/z calcd for C$_{31}$H$_{33}$N$_2$O$_4$: 517.2503 [M+H]$^+$. found: 517.2499.

3-tert-Butoxycarbonylamino-2-(fluoren-9-ylidene-amino)-3-furan-2-yl-propio nic acid tert-butyl eater

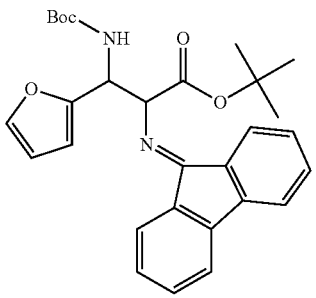 [SMILES: CC(C)(C)OC(=O)NC(c1ccco1)C(N=C1c2ccccc2-c2ccccc21)C(=O)OC(C)(C)C]

mp: 159.5-161.5° C. IR(KBr): 3400, 2978, 1718, 1492, 1149 cm$^{-1}$. $^1$H NMR (CDCl$_3$): δ 1.47 (s, 9H), 1.48 (s, 9H), 5.45 (s, 1H), 5.73 (d, J=8.9 Hz, 1H), 6.08 (d, J=8.2 Hz, 1H), 6.18 (t, J=6.9 Hz, 2H), 7.21-7.26 (m, 9H), 7.83 (d, J=7.6 Hz, 1H).
$^{13}$C NMR (CDCl$_3$): δ 27.9, 28.4, 51.9, 66.4, 79.6, 82.9, 106.6, 110.3, 119.3, 120.5, 123.2, 126.7, 128.0, 128.3, 131.4, 131.8, 138.1, 141.2, 141.7, 144.1, 154.0, 155.2, 166.8, 167.8.

FAB-HRMS m/z calcd for C$_{29}$H$_{32}$N$_2$O$_5$: 489.2389 [M+H]$^+$. found: 489.2421.

3-tert-Butoxycarbonylamino-2-(fluoren-9-ylidene-amino)-5-phenyl-pentanoic acid tert-butyl ester

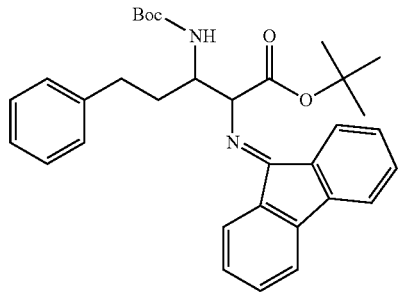 [SMILES: CC(C)(C)OC(=O)NC(CCc1ccccc1)C(N=C1c2ccccc2-c2ccccc21)C(=O)OC(C)(C)C]

mp: 154-156° C. IR(KBr): 3430, 2978, 1721, 1492, 1167 cm$^{-1}$. $^1$H NMR (CDCl$_3$): δ 1.47 (s, 18H), 1.81 (t, J=5.2 Hz, 1H), 1.91 (t, J=5.2 Hz, 1H), 2.70 (q, J=5.5 Hz, 1H), 2.74 (t, J=5.3 Hz, 1H), 4.56 (d, J=5.5 Hz, 1H), 4.98 (d, J=1.1 Hz, 1H), 5.70 (t, J=9.6 Hz, 1H), 7.31 (m, 7H), 7.40-7.43 (m, 2H), 7.53-7.56 (m, 2H), 7.64 (d, J=7.6 Hz, 1H), 7.88 (d, J=7.6 Hz, 1H).
$^{13}$C NMR (CDCl$_3$): δ 27.9, 28.3, 28.4, 32.6, 36.2, 53.3, 6.2, 79.0, 82.5, 119.3, 120.5, 123.2, 125.7, 126.6, 127.9, 128.3, 128.35, 128.43, 128.47, 131.4, 131.7, 131.8, 138.1, 141.2, 141.9, 144.1, 155.6, 166.8, 168.7.
ESI-FIRMS m/z calcd for C$_{33}$H$_{38}$N$_2$O$_4$: 527.2910 [M+H]$^+$. found: 527.2936.

2) Asymmetric Synthesis of Diamino Acid Ester

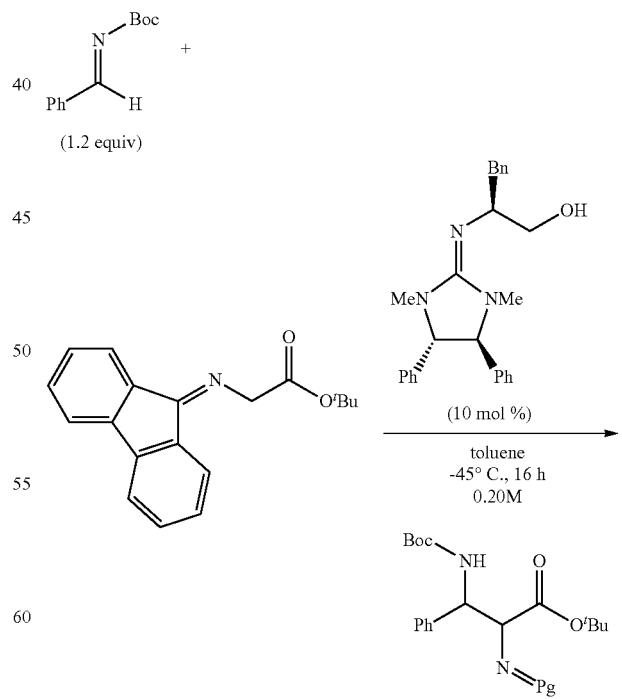

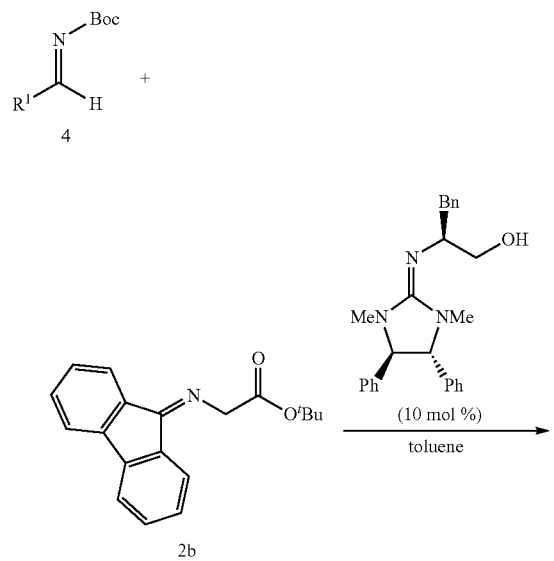

| entry | $R^1$ | temp/°C | time/h | yield/% | syn/anti | ee (syn) |
|---|---|---|---|---|---|---|
| 1 | Ph | −45 | 12 | quant | >99/1 | 96 (2S,3R) |
| 2 | Ph | −60 | 12 | quant | >99/1 | 95 (2S,3R) |
| 3 | p-MeOC$_6$H$_4$ | −45 | 48 | 76 | 36/1 | 90 |
| 4 | 2-Furyl | −45 | 36 | 88 | 9/1 | 98 |
| 5 | Ph(CH$_2$)$_2$ | −46 | 24 | 87 | 29/1 | 92 |
| 6 | c-C$_6$H$_{11}$ | −45 | 48 | 84 | 11/1 | 96 |

[A General Manipulation]

Chiral guanidine derivatives (8.0 mg, 0.020 mmol) and a toluene solution (0.60 mL) of the glycine Schiff base (58.7 mg, 0.20 mmol) were stirred at −45° C. A toluene solution (0.40 mL) of the imine (49.3 mg, 0.24 mmol) was added during this stirring-up. And, the stirring-up was conducted for 16 hours at −45° C. Thereafter, the saturated ammonium chloride aqueous solution was added, and the reaction was stopped. And, the temperature was raised (to the room temperature). Thereafter, the extraction from the water phase was carried out with the methylene chloride three times. And, the organic phase was collected, and dried by using the anhydrous sodium sulfate. After the filtering and the concentration under reduced pressure, the obtained crude product was refined with the thin-layer silica gel chromatography (hexane/acetone=4/1). With this, the target product was obtained. The diastereomer ratio was determined with the HPLC analysis.

3) Synthesis of the Diamino Phosphonic Acid Ester Derivatives

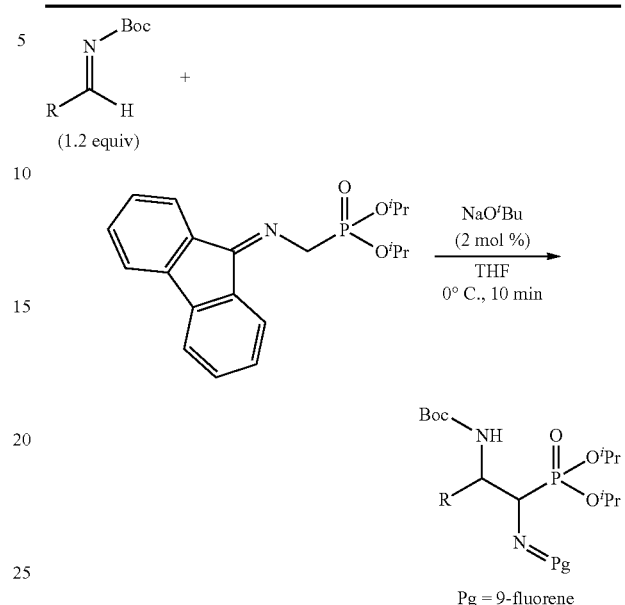

| entry | R | yield (%) | syn/anti |
|---|---|---|---|
| 1 | Ph | 95 | >50/1 |
| 2 | p-MeOC$_6$H$_4$ | quant | 12.9/1 |
| 3 | p-FC$_6$H$_4$ | 97 | 27.4/1 |
| 4 | m-MeC$_6$H$_4$ | 96 | 21.7/1 |
| 5 | o-MeC$_6$H$_4$ | 99 | >99/1 |
| 6[a] | m-vinylC$_6$H$_4$ | quant | >50/1 |
| 7 | 2-Furyl | quant | 23.4/1 |
| 8[b] | 2-Thienyl | quant | 32.9/1 |
| 9[b] | Ph(CH$_2$)$_2$ | 88 | >99/1 |
| 10[b] | Cyclohexyl | quant | >99/1 |

[a] 16 h.
[b] 2.0 equiv of imine.

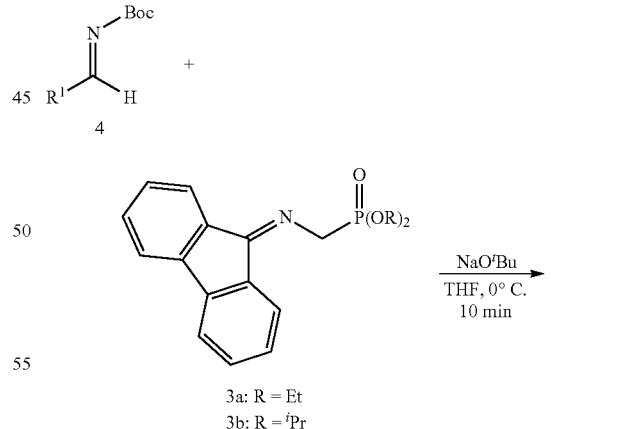

3a: R = Et
3b: R = $^i$Pr

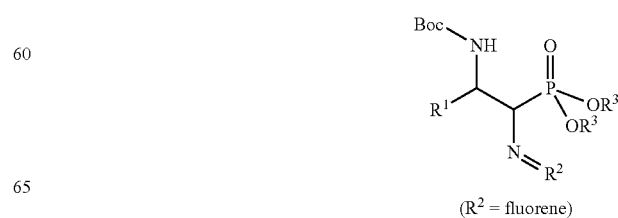

($R^2$ = fluorene)

-continued

| entry | GlyP | R[1] | catalyst (mol %) | yield/% | syn/anti[b] |
|---|---|---|---|---|---|
| 1 | 3a | Ph | NaO$^t$Bu (10) | 94 | 13/1 |
| 2 | 3b | Ph | NaO$^t$Bu (2) | 95 | >99/1 |
| 3 | 3b | o-MeC$_6$H$_4$ | NaO$^t$Bu (2) | 99 | >99/1 |
| 4 | 3b | m-vinylC$_6$H$_4$ | NaO$^t$Bu (2) | quant | >99/1 |
| 5 | 3b | 2-Furyl | NaO$^t$Bu (2) | quant | 23/1 |
| 6 | 3b | 2-Thienyl | NaO$^t$Bu (2) | quant | 33/1 |
| 7 | 3b | Ph(CH$_2$)$_2$ | NaO$^t$Bu (2) | 88 | >99/1 |
| 8 | 3b | c-C$_6$H$_{11}$ | NaO$^t$Bu (2) | quant | >99/1 |

3-1) Synthesis of the Glycine Schiff Base Phosphonic Acid Derivatives Fluorene imine hydrochloride (5.0 g, 46.7 mmol) and aminomethyl phosphonic acid ester (7.8 g, 46.7 mmol) were stirred in the methylene chloride for 24 hours at room temperature. The reaction solution was filtered with the celite. Thereafter, the solvent was removed by the distillation under reduced pressure. The obtained residual was allowed to dissolve in the diethyl ether. And, it was filtered with the celite. The obtained ether solution was cleaned with water and a saturated sodium chloride aqueous solution. And, it was dried over the sodium sulfate. After the filtering and the concentration under reduced pressure, the obtained crude product was refined with a neutral silica gel column chromatography (hexane/acetone=4/1). (Fluoren-9-ylideneaminomethyl)-phosphonic acid diethyl ester (6.3 g, 61%) was obtained with the cleaning by the hexane.

(Fluoren-9-ylideneaminomethyl)-phosphonic acid diethyl ester

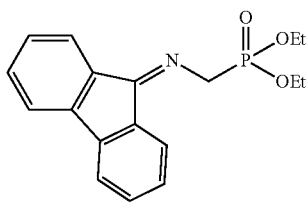 [SMILES: CCOP(=O)(CN=C1c2ccccc2-c2ccccc21)OCC]

mp: 70-71° C. IR(KBr): 2979, 1646, 1452, 1243, 1031, 974 cm$^{-1}$. $^1$H NMR (CDCl$_3$): δ 1.35 (t, J=7.1 Hz, 6H), 4.27 (m, 4H), 4.71 (d, J=16.4 Hz, 2H), 7.22-7.30 (m, 2H), 7.40-7.44 (m, 2H), 7.56 (d, J=7.4 Hz, 1H), 7.65 (d, J=7.4 Hz, 1H), 7.79 (d, J=7.4 Hz, 1H), 7.91 (d, J=7.9 Hz, 1H).
$^{13}$C NMR (CDCl$_3$): δ 16.5, 16.6, 50.1, 51.4, 62.7, 62.8, 119.3, 120.5, 122.9, 127.46, 127.48, 128.1, 128.4, 131.2, 131.7, 131.8, 138.2, 138.3, 141.0, 143.9, 166.1, 166.2.
$^{31}$P NMR (CDCl$_3$H$_3$PO$_4$ δ0.00): δ 22.7
ESI-HRMS m/z calcd for C$_{18}$H$_{20}$NO$_3$P: 330.1259 [M+H]$^+$. found: 330.1251.

(Fluoren-9-ylideneaminomethyl)-phosphonic acid diisopropyl ester

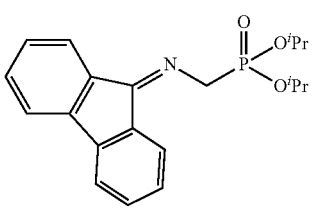 [SMILES: CC(C)OP(=O)(CN=C1c2ccccc2-c2ccccc21)OC(C)C]

mp: 102.5-104.5° C. IR(KBr): 2986, 1648, 1602, 1450, 1221, 987 cm$^{-1}$. $^1$H NMR (CDCl$_3$): δ 1.34-1.37 (m, 12H), 4.66 (d, J=16.5 Hz, 2H), 4.87-4.90 (m, 2H), 7.29 (t, J=7.6 Hz, 2H), 7.40 (t, J=7.6 Hz, 1H), 7.44 (t, J=7.6 Hz, 1H), 7.56 (d, J=7.6 Hz, 1H), 7.65 (d, J=7.6 Hz, 1H), 7.79 (d, J=7.6 Hz, 1H), 7.93 (d, J=8.2 Hz, 1H).
$^{13}$C NMR (CDCl$_3$): δ 24.0, 24.1, 24.18, 24.20, 50.8, 51.9, 71.29, 71.33, 119.3, 120.4, 122.9, 127.5, 128.0, 128.3, 131.1, 131.7, 131.8, 138.4, 141.0, 143.8, 165.8, 165.9.
$^{31}$P NMR (CDCl$_3$H$_3$PO$_4$ δ0.00): δ 21.0
ESI-HRMS m/z calcd for C$_{20}$H$_{24}$NO$_3$P: 358.1572 [M+H]$^+$. found: 358.1567.

({[Bis-(4-trifluoromethyl-phenyl)-methylene]-amino}-methyl)-phosphonic acid diethyl ester

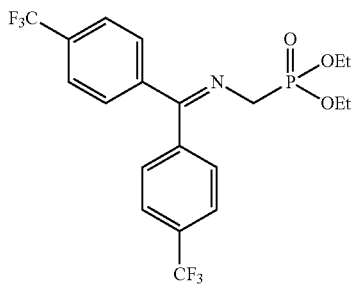 [SMILES: CCOP(=O)(CN=C(c1ccc(C(F)(F)F)cc1)c1ccc(C(F)(F)F)cc1)OCC]

mp: 78.5-82° C. IR(KBr): 2982, 1635, 1325 cm$^{-1}$. $^1$H NMR (CDCl$_3$): δ 1.35 (t, J=7.2 Hz, 3H), 3.92 (d, J=17.9 Hz, 2H), 4.18-4.20 (m, 4H), 7.41 (d, J=7.6 Hz, 2H), 7.61 (d, J=8.2 Hz, 2H), 7.72 (d, J=8.2 Hz, 2H), 7.79 (d, J=8.2 Hz, 2H).
$^{13}$C NMR (CDCl$_3$): δ 16.3, 16.39, 16.43, 16.51, 16.54, 16.6, 51.2, 51.3, 52.4, 62.37, 62.42, 62.5, 62.6, 62.68, 62.71, 122.9, 125.1, 125.2, 125.9, 128.4, 128.5, 128.6, 128.8, 131.2, 132.2, 132.4, 138.3, 141.6, 169.1, 169.2.
$^{31}$P NMR (CDCl$_3$H$_3$PO$_4$ δ 0.00): δ 22.5
ESI-HRMS m/z calcd for C$_{32}$H$_{38}$FN$_2$O$_5$P: 581.2575 [M+H]$^+$. found: 581.2570.

Bis[4-(trifluoromethyl)phenyl]methanimine

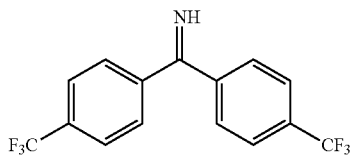 [SMILES: N=C(c1ccc(C(F)(F)F)cc1)c1ccc(C(F)(F)F)cc1]

One part of 4-bromobenzotrifluoride (12.4 g, 55 mmol) and a small quantity of iodine were added to an Et$_2$O suspension (10 mL) of magnesium (1.34 g, 55 mmol) under an argon atmosphere. And, they were heated appropriately. After the reaction start was observed, the remaining Et$_2$O solution (15 mL) of the remaining 4-bromobenzotrifluoride was added slowly. After heat refluxing for one hour, a toluene solution (10 mL) of 4-(trifluoromethyl)benzonitrile (11.8 g, 86 mmol) was added slowly at room temperature. After heat refluxing for 20 hours, anhydrous methanol (12 mL) was added slowly at room temperature. And, the stirring-up was conducted for thirty minutes. Insoluble compounds were removed with the celite filtering. The filtrate was concentrated under reduced pressure. Thereafter, the obtained crude product was distillated under reduced pressure. And, the target product (11.9 g, 75%) was obtained. After distillation, the product was solidified.

Bp: 115° C. (0.30 mmHg).

$^1$H NMR (CDCl$_3$): δ 7.53-7.84 (m, 8H), 10.1 (s, 1H).

$^{13}$C NMR (CDCl$_3$): δ 123.8 (q, J=278.9 Hz), 125.4, 125.9, 127.9, 129.5, 132.2-132.9 (m), 140.9, 142.9, 175.9.

3-2) A General Manipulation of Synthesizing the Diamino Phosphonic Acid Ester Derivatives Typical experimental procedure for the reaction of (fluoren-9-ylideneaminomethyl)-phosphonic acid diethyl ester with Boc-imine A THF solution (0.4 mL) of the glycine Schiff base phosphorus analogues (0.2 mmol) was stirred at 0° C. under an argon atmosphere. A solution (0.1 mL) containing THF and NaO$^t$Bu (NaO$^t$Bu: THF=0.04 mmol: 1.0 mL), and a THF solution (0.50 mL) of the imines (0.24 mmol) were sequentially added. The stirring-up was conducted for 10 minutes at 0° C. Thereafter, the reaction was stopped by adding a saturated ammonium chloride aqueous solution. And, the temperature was raised (to the room temperature). The extraction from the water phase was carried out with the methylene chloride three times. And, the organic phase was collected, and dried by using the anhydrous sodium sulfate. After the filtering and the concentration under reduced pressure, the obtained crude product was refined with the thin-layer silica gel chromatography (hexane/acetone=2/1). With this, the target product was obtained. The diastereomer ratio was determined with a $^{31}$P-NMR ratio.

[2-tert-Butoxycarbonylamino-1-(fluoren-9-ylidene-amino)-2-phenyl-ethyl]-ph osphonic acid diethyl ester

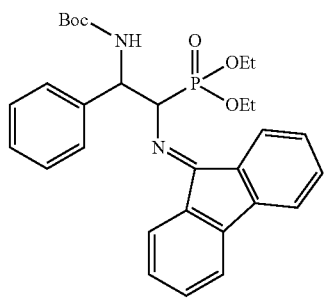 [SMILES: CCOP(=O)(OCC)C(N=C1c2ccccc2-c2ccccc21)C(NC(=O)OC(C)(C)C)c1ccccc1]

mp: 113-115° C. IR(KBr): 2976, 1713, 1250, 1171, 1018 cm$^{-1}$. $^1$H NMR (DMSO-d$_6$) syn isomer: δ 0.97 (t, J=7.2 Hz, 3H), 1.03 (t, J=7.2 Hz, 3H), 1.32 (s, 9H), 3.79-3.89 (m, 3H), 3.91-3.94 (m, 1H), 5.37-5.43 (m, 2H), 7.15 (t, J=7.2 Hz, 1H), 7.24 (t, J=7.9 Hz, 3H), 7.32-7.36 (m, 2H), 7.39-7.40 (m, 2H), 7.47-7.50 (m, 2H), 7.76 (d, J=6.9 Hz, 1H), 7.83 (d, J=7.6 Hz, 1H), 7.86 (t, J=6.9 Hz, 2H).

anti isomer: δ 1.07-1.10 (m, 6H), 1.37 (s, 9H), 3.92-4.01 (m, 4H), 5.33 (d, J=11.0 Hz, 1H), 5.53-5.56 (m, 1H), 7.02 (t, J=7.2 Hz, 1H), 7.10 (t, J=7.9 Hz, 2H), 7.28 (t, J=7.2 Hz, 1H), 7.36 (t, J=8.2 Hz, 3H), 7.42 (t, J=7.6 Hz, 1H), 7.47-7.52 (m, 2H), 7.61 (d, J=8.9 Hz, 1H), 7.70 (d, J=7.6 Hz, 1H), 7.79 (d, J=7.6 Hz, 1H), 8.08 (d, J=7.6 Hz, 1H).

$^{13}$C NMR (DMSO-d$_6$) syn isomer: δ 15.89, 15.91, 27.9, 28.1, 55.8, 61.77, 61.81, 62.09, 62.13, 64.4, 65.3, 77.9, 119.7, 120.5, 122.7, 126.9, 127.1, 127.3, 127.7, 127.8, 127.9, 128.1, 128.3, 131.1, 131.5, 131.8, 137.6, 140.2, 141.08, 141.12, 143.1, 154.6, 164.5, 164.6.

anti isomer (detectable peaks): δ 16.0, 28.1, 56.1, 59.1, 61.88, 61.92, 62.1, 62.2, 63.3, 63.9, 64.3, 72.8, 77.8, 81.1, 119.7, 120.6, 122.1, 126.7, 127.3, 127.7, 128.1, 128.3, 131.1, 131.3, 131.7, 137.5, 140.0, 142.3, 154.3.

$^{31}$P NMR (DMSO-d$_6$H$_3$PO$_4$ δ0.00): δ 20.5 (major), 21.1 (minor)

FAB-HRMS m/z calcd for C$_{30}$H$_{36}$N$_2$O$_5$P: 535.2362 [M+H]$^+$. found: 535.2372. A*nal. Calcd* for C$_{30}$H$_{35}$N$_2$O$_5$P: C, 67.40; H, 6.60; N, 5.24. found: C, 65.43; H, 6.91; N, 4.61.

[2-tert-Butoxycarbonylamino-1-fluoren-9-ylidene-amino)-2-phenyl-ethyl]-ph osphonic acid diisopropyl ester

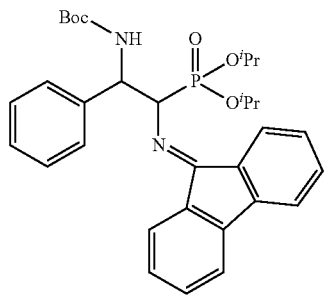 [SMILES: CC(C)OP(=O)(OC(C)C)C(N=C1c2ccccc2-c2ccccc21)C(NC(=O)OC(C)(C)C)c1ccccc1]

mp: 110-112° C. IR(KBr): 3428, 2979, 1724, 1488, 987 cm$^{-1}$. $^1$H NMR (DMSO-d$_6$): δ 0.92 (d, J=5.5 Hz, 3H), 1.09-1.15 (m, 9H), 1.33 (s, 9H), 4.42-4.48 (m, 2H), 5.31 (dd, J=5.5, 15.1 Hz, 2H), 5.42 (d, J=6.2 Hz, 1H), 7.10-7.15 (m, 2H), 7.72 (t, J=7.6 Hz, 2H), 7.30-7.38 (m, 4H), 7.46-7.49 (m, 2H), 7.76 (d, J=7.6 Hz, 1H), 7.77-85 (m, 3H).

$^{13}$C NMR (DMSO-d$_6$): δ 23.15, 23.19, 23.23, 23.7, 23.8, 27.9, 28.1, 55.9, 64.6, 65.6, 70.57, 70.62, 70.66, 70.71, 77.8, 119.7, 120.5, 122.6, 126.8, 127.2, 127.3, 127.7, 127.8, 127.97, 128.04, 128.3, 131.2, 131.4, 131.8, 137.6, 140.2, 141.27, 141.31, 143.1, 154.5, 164.5, 164.6.

31P NMR (DMSO-d$_6$H$_3$PO$_4$ δ0.00): δ 18.6 (major), 19.7 (minor)

ESI-HRMS m/z calcd for C$_{32}$H$_{39}$N$_2$O$_5$P: 563.2669 [M+H]$^+$. found: 563.2638.

Anal. Calcd for C$_{32}$H$_{39}$N$_2$O$_5$P: C, 68.31; H, 6.99; N, 4.98. found: C, 68.27; H, 7.11; N, 4.88.

[2-tert-Butoxycarbonylamino-1-(fluoren-9-ylidene-amino)-2-(4-methoxy-phen yl)-ethyl]-phosphonic acid diisopropyl ester

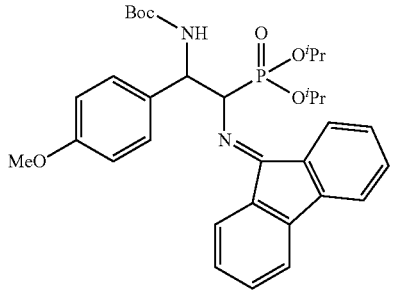 [SMILES: COc1ccc(C(NC(=O)OC(C)(C)C)C(N=C2c3ccccc3-c3ccccc32)P(=O)(OC(C)C)OC(C)C)cc1]

mp: 67-72° C. IR(KBr): 3436, 2978, 1717, 987 cm$^{-1}$. $^1$H NMR (DMSO-d$_6$): δ 0.92 (d, J=6.2 Hz, 3H), 1.10-1.15 (m, 9H), 1.32 (s, 9H), 3.65 (s, 3H), 4.42-4.49 (m, 2H), 5.27 (dd,

J=5.5, 15.1 Hz, 1H), 5.37 (d, J=6.2 Hz, 1H), 6.79 (d, J=8.2 Hz, 2H), 7.08 (d, J=8.9 Hz, 1H), 7.27-7.37 (m, 4H), 7.46-7.50 (m, 2H), 7.76-7.86 (m, 4H).
$^{13}$C NMR (DMSO-d$_6$): δ 23.3, 23.8, 23.9, 28.2, 54.9, 55.3, 64.9, 65.9, 70.6, 70.69, 70.74, 77.8, 112.7, 113.3, 119.8, 120.6, 122.6, 128.1, 128.4, 128.5, 131.3, 131.5, 131.8, 133.4, 137.7, 140.2, 143.2, 154.6, 158.2, 164.46, 164.55.
$^{31}$P NMR (DMSO-d$_6$H$_3$PO$_4$ δ0.00): δ 18.8 (major), 19.8 (minor) ESI-HRMS m/z calcd for C$_{33}$H$_{41}$N$_2$O$_6$P): 593.2775 [M+H]$^-$. found: 593.2788.

[2-tert-Butoxycarbonylamino-1-(fluoren-9-ylidene-amino)-2-(4-fluoro-phenyl)-ethyl]-phosphonic acid diisopropyl ester

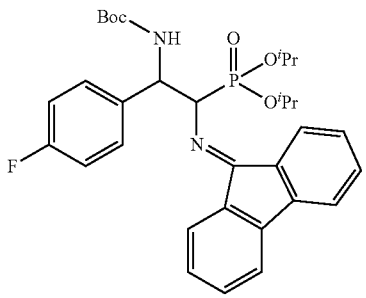 [SMILES: CC(C)OP(=O)(OC(C)C)C(N=C1c2ccccc2-c2ccccc21)C(NC(=O)OC(C)(C)C)c1ccc(F)cc1]

mp: 69-73° C. IR(KBr): 3435, 2979, 1717, 1489, 986 cm$^{-1}$. $^1$H NMR (DMSO-d$_6$): δ 0.89-1.15 (m, 12H), 1.15 (s, 9H), 4.42-4.48 (m, 2H), 5.28-5.41 (m, 1H), 5.42 (d, J=6.9 Hz, 1H), 7.06-7.09 (m, 2H), 7.19 (d, J=11.1 Hz, 1H), 7.32-7.51 (m, 6H), 7.77-7.86 (m, 4H).
$^{13}$C NMR (DMSO-d$_6$): δ 23.18, 23.24, 23.7, 23.8, 28.1, 55.6, 64.7, 65.7, 70.6, 70.79, 70.83, 77.9, 114.5, 114.6, 119.8, 120.6, 122.6, 128.1, 128.4, 129.56, 129.61, 131.3, 131.5, 131.9, 137.5, 137.7, 140.2, 143.2, 154.6, 160.5, 162.1, 164.6, 164.7.
$^{31}$P NMR (DMSO-d$_6$H$_3$PO$_4$ δ0.00): δ 18.6 (major), 19.4 (minor) ESI-HRMS m/z calcd for C$_{32}$H$_{38}$FN$_2$O$_5$P: 581.2575 [M+H]$^+$. found: 581.2570.

[2-tert-Butoxycarbonylamino-1-(fluoren-9-ylidene-amino)-2-m-tolyl-ethyl]-phosphonic acid diisopropyl ester

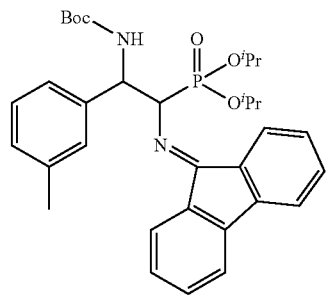 [SMILES: Cc1cccc(C(NC(=O)OC(C)(C)C)C(N=C2c3ccccc3-c3ccccc32)P(=O)(OC(C)C)OC(C)C)c1]

mp: 51-57.5° C. IR(KBr): 3437, 2978, 1717, 1489, 958 cm$^{-1}$. $^1$H NMR (DMSO-d$_6$): δ 0.93 (d, J=5.5 Hz, 3H), 1.10-1.16 (m, 9H), 1.33 (s, 9H), 2.19 (s, 3H), 4.43-4.49 (m, 2H), 5.28 (dd, J=5.5, 14.4 Hz, 1H), 5.38 (d, J=6.2 Hz, 1H), 6.94 (d, J=7.6 Hz, 1H), 7.06-7.19 (m, 4H), 7.30-7.37 (m, 2H), 7.46-7.49 (m, 2H), 7.76 (d, J=7.6 Hz, 1H), 7.81-7.85 (m, 3H).
$^{13}$C NMR (DMSO-d$_6$): δ 21.0, 23.3, 23.7, 23.9, 28.2, 55.9, 64.6, 65.6, 70.7, 77.9, 119.0, 120.6, 122.6, 124.3, 127.5, 127.8, 128.0, 128.1, 128.2, 128.4, 131.2, 131.5, 131.8, 136.7, 137.7, 140.2, 141.3, 143.1, 154.6, 164.5 164.6.
31P NMR (DMSO-d$_6$H$_3$PO$_4$ δ0.00): δ 18.7 (major), 19.8 (minor) ESI-HRMS m/z calcd for C$_{33}$H$_{41}$N$_2$O$_5$P: 577.2826 [M+H]$^+$. found: 577.2832.

[2-tert-Butoxycarbonylamino-1-(fluoren-9-ylidene-amino)-2-o-tolyl-ethyl]-pho sphonic acid diisopropyl ester

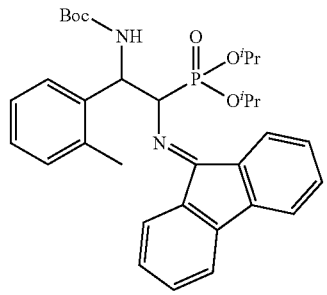 [SMILES: Cc1ccccc1C(NC(=O)OC(C)(C)C)C(N=C1c2ccccc2-c2ccccc21)P(=O)(OC(C)C)OC(C)C]

mp: 58.5-63° C. IR(KBr): 3435, 2978, 1716, 1488, 984 cm$^{-1}$. $^1$H NMR (DMSO-d$_6$): δ 0.90 (d, J=5.5 Hz, 3H), 1.10-1.24 (m, 9H), 1.33 (s, 9H), 4.43-4.50 (m, 2H), 5.21 (dd, J=5.2, 14.8 Hz, 1H), 5.74-5.76 (m, 1H), 6.99-7.03 (m, 2H), 7.08-7.11 (m, 2H), 7.29-7.38 (m, 3H), 7.46-7.50 (m, 2H), 7.73-7.88 (m, 4H).
$^{13}$C NMR (DMSO-d$_6$): δ 19.1, 23.3, 23.7, 23.9, 28.2, 51.4, 63.4, 64.4, 70.7, 70.8, 77.9, 119.8, 120.6, 122.7, 125.5, 126.7, 127.2, 127.8, 128.2, 128.5, 129.8, 131.3, 131.6, 131.9, 134.5, 137.7, 140.0, 140.3, 143.2, 154.7, 164.86, 164.94.
$^{31}$P NMR (DMSO-d$_6$H$_3$PO$_4$ δ0.00): δ 18.7 (major), 20.1 (minor) ESI-HRMS m/z calcd for C$_{33}$H$_{41}$N$_2$O$_5$P: 577.2826 [M+H]$^+$. found: 577.2843.

[2-tert-Butoxycarbonylamino-1-(fluoren-9-ylidene-amino)-2-(3-vinyl-phenyl)-ethyl]-phosphonic acid diisopropyl ester

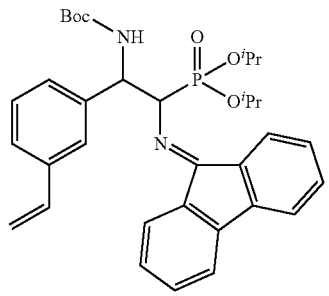 [SMILES: C=Cc1cccc(C(NC(=O)OC(C)(C)C)C(N=C2c3ccccc3-c3ccccc32)P(=O)(OC(C)C)OC(C)C)c1]

mp: 52-56° C. IR(KBr): 3430, 2979, 1719, 1489, 986 cm$^{-1}$. $^1$H NMR (DMSO-d$_6$): δ 0.93 (d, J=6.2 Hz, 3H), 1.14-1.15 (m, 9H), 1.33 (s, 9H), 4.42-4.50 (m, 2H), 5.18 (d, J=11.0 Hz, 1H), 5.31 (dd, J=5.5, 15.1 Hz, 1H), 5.40-5.42 (m, 1H), 5.71 (d, J=17.9 Hz, 1H), 6.63 (dd, J=11.0, 17.2 Hz, 1H), 7.15-7.24 (m, 3H), 7.28-7.36 (m, 3H), 7.46-7.51 (m, 3H), 7.75-7.88 (m, 4H).

$^{13}$C NMR (DMSO-d$_6$): δ 23.2, 23.6, 23.7, 28.1, 55.8, 64.5, 65.5, 70.57, 70.63, 70.7, 77.8, 114.0, 119.7, 120.5, 122.6, 124.9, 125.2, 126.9, 128.0, 128.1, 128.3, 131.2, 131.4, 131.8, 136.5, 137.6, 140.1, 141.5, 141.6, 143.1, 154.6, 164.5, 164.6.
$^{31}$P NMR (DMSO-d$_6$H$_3$PO$_4$ δ0.00): δ 18.6 (major) ESI-HRMS m/z calcd for C$_{34}$H$_{41}$N$_2$O$_5$P: 589.2826[M+H]$^-$. found: 589.2840.

[2-tert-Butoxycarbonylamino-1-(fluoren-9-ylidene-amino)-2-furan-2-yl-ethyl]-phosphonic acid diisopropyl ester

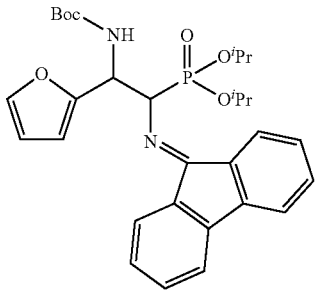 [SMILES: CC(C)OP(=O)(OC(C)C)C(N=C1c2ccccc2-c2ccccc21)C(NC(=O)OC(C)(C)C)c1ccco1]

mp: 44-46.5° C. IR(KBr): 3437, 2979, 1719, 1491, 987 cm$^{-1}$. $^1$H NMR (DMSO-d$_6$): δ 1.00 (d, J=6.2 Hz, 3H), 1.15-1.28 (m, 9H), 1.34 (s, 9H), 4.49-4.52 (m, 2H), 5.41 (dd, J=5.2, 14.8 Hz, 1H), 5.50 (br s, 1H), 6.17 (d, J=2.7 Hz, 1H), 6.28 (t, J=2.4 Hz, 1H), 7.01 (d, J=8.9 Hz, 1H), 7.32-7.39 (m, 2H), 7.47-7.53 (m, 3H), 7.77-7.78 (m, 2H), 7.86 (d, J=7.6 Hz, 1H), 7.91 (d, J=8.2 Hz, 1H).
$^{13}$C NMR (DMSO-d$_6$): δ 22.6, 23.3, 23.4, 23.7, 23.8, 28.0, 50.0, 62.2, 63.2, 70.7, 70.71, 70.84, 70.9, 78.0, 106.7, 110.3, 119.8, 120.6, 122.7, 127.9, 128.2, 128.3, 131.2, 131.5, 131.9, 137.6, 140.2, 141.8, 143.2, 153.4, 153.46, 153.50, 154.6, 164.7, 164.8.
$^{31}$P NMR (DMSO-d$_6$ H$_3$PO$_4$ δ0.00): δ 18.0 (major), 19.3 (minor) ESI-HRMS m/z calcd for C$_{30}$H$_{37}$N$_2$O$_6$P: 553.2462 [M+H]$^+$. found: 553.2480.

[2-tert-Butoxycarbonylamino-1-(fluoren-9-ylidene-amino)-2-thiophen-2-yl-ethyl]-phosphonic acid diisopropyl ester

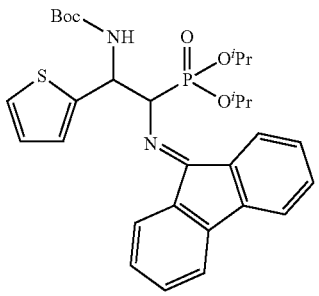 [SMILES: CC(C)OP(=O)(OC(C)C)C(N=C1c2ccccc2-c2ccccc21)C(NC(=O)OC(C)(C)C)c1cccs1]

mp: 60-65° C. IR(KBr): 3437, 1719, 1491, 987 cm$^{-1}$. $^1$H NMR (DMSO-d$_6$): δ 1.03 (d, J=6.2 Hz, 3H), 1.16-1.20 (m, 9H), 1.38 (s, 9H), 4.51-4.55 (m, 2H), 5.44 (dd, J=4.1, 15.8 Hz, 1H), 5.67 (br d, J=3.4 Hz, 1H), 6.84-6.86 (m, 1H), 7.00 (d, J=4.1 Hz, 2H), 7.25 (d, J=4.8 Hz, 1H), 7.32-7.37 (m, 2H), 7.47-7.51 (m, 2H), 7.77 (d, J=7.6 Hz, 1H), 7.82-7.85 (m, 2H), 7.98 (d, J=8.2 Hz, 1H).

$^{13}$C NMR (DMSO-d$_6$): δ 23.4, 23.8, 23.9, 28.1, 51.4, 64.3, 65.3, 70.9, 70.91, 71.00, 71.05, 78.3, 119.9, 120.6, 122.8, 124.7, 124.8, 126.5, 128.2, 128.5, 131.2, 131.7, 132.1, 137.6, 140.3, 143.3, 145.2, 145.3, 154.5, 165.1, 165.2.
$^{31}$P NMR (DMSO-d$_6$H$_3$PO$_4$ δ0.00): δ 17.9 (major), 19.0 (minor) ESI-HRMS m/z calcd for C$_{30}$H$_{37}$N$_2$O$_5$PS: 569.2234 [M+H]$^+$. found: 569.2237.

[2-tert-Butoxycarbonylamino-1-(fluoren-9-ylidene-amino)-4-phenyl-butyl]-phosphonic acid diisopropyl ester

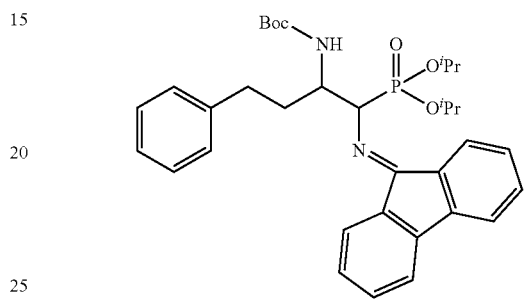

mp: 124-131° C. IR(KBr): 3292, 2978, 1711, 990 cm$^{-1}$. $^1$H NMR (DMSO-d$_6$): δ 1.01 ((d, J=6.2 Hz, 3H), 1.16-1.21 (m, 9H), 1.30 (s, 9H), 1.79 (br, 1H), 2.01 (br, 1H), 2.01 (br, 1H), 2.63 (br, 1H), 4.21 (s, 1H), 4.55 (d, J=5.5 Hz, 2H), 5.10 (d, J=6.6 Hz, 3H), 6.45 (d, J=8.9 Hz, 1H), 7.12-7.53 (m, 9H), 7.73 (d, J=7.6 Hz, 1H), 7.78 (d, J=7.6 Hz, 1H), 7.87 (d, J=7.6 Hz, 1H), 8.04 (d, J=8.2 Hz, 1H).
$^{13}$C NMR (DMSO-d$_6$): δ 23.36, 23.41, 23.8, 23.9, 28.0, 28.1, 28.2, 28.3, 31.9, 34.5, 51.8, 51.9, 70.6, 70.7, 70.8, 77.5, 99.4, 119.7, 119.80, 120.6, 122.6, 122.7, 125.5, 125.7, 128.07, 128.12, 128.30, 128.33, 131.2, 131.3, 131.8, 131.9, 137.8, 140.3, 141.7, 143.2, 155.1, 164.0, 164.1.
$^{31}$P NMR (DMSO-d$_6$H$_3$PO$_4$ δ0.00): δ 19.6 (major) ESI-HRMS m/z calcd for C$_{34}$H$_{43}$N$_2$O$_5$P: 591.2982[M+H]$^+$. found: 591.2992.

[2-tert-Butoxycarbonylamino-2-cyclohexyl-1-(fluoren-9-ylideneamino)-ethyl]-phosphonic acid diisopropyl eater

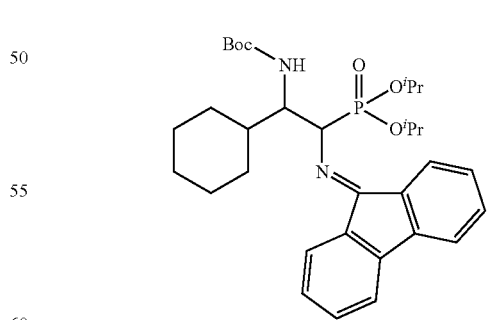

mp: 66-70° C. IR(KBr): 3438, 2978, 1716, 1492, 986 cm$^{-1}$. $^1$H NMR (DMSO-d$_6$): δ 0.85-1.69 (m, 32H), 4.12-4.17 (m, 1H), 4.51-4.58 (m, 2H), 5.18 (dd, J=4.8, 16.5 Hz, 1H), 6.29 (d, J=9.6 Hz, 1H), 7.33-7.54 (m, 4H), 7.74-7.97 (m, 4H).
$^{13}$C NMR (DMSO-d$_6$): δ 23.4 8 23.5, 23.8, 23.9, 25.5, 25.7, 25.9, 27.8, 28.1, 28.2, 29.7, 40.39, 40.43, 55.7, 60.3, 61.3, 70.7, 77.4, 119.9, 120.7, 122.6, 128.1, 128.3, 128.4, 131.4, 131.5, 131.9, 137.7, 140.3, 143.2, 155.3, 164.2.
$^{31}$P NMR (DMSO-d$_6$H$_3$PO$_4$ δ0.00): δ 19.8 (major) ESI-HRMS m/z calcd for C$_{32}$H$_{45}$N$_2$O$_5$P: 569.3139[M+H]$^+$. found: 569.3149.

This application is based upon and claims the benefit of priority from Japanese patent application No. 2008-58993, filed on Mar. 10, 2008, the disclosure of which is incorporated herein in its entirety by reference.

The invention claimed is:

1. A method of manufacturing a compound of formula [IV]:

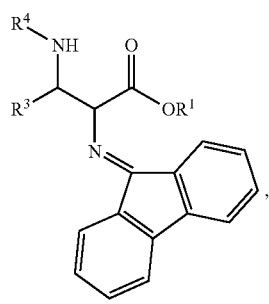

formula [IV]

wherein
R$^1$ is a substituted hydrocarbon group or an unsubstituted hydrocarbon group,
R$^3$ is a substituted hydrocarbon group, a substituted heterocyclic group, an unsubstituted hydrocarbon group, or an unsubstituted heterocyclic group,
R$^4$ is an electron-withdrawing group, and
the fluorenyl group is a ring-substituted fluorenyl group or a ring-unsubstituted fluorenyl group,
the method comprising reacting a compound of formula [III]:

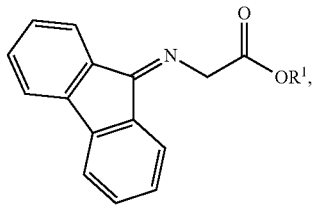

formula [III]

with a compound of formula [V]:

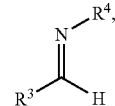

formula [V]

wherein
R$^3$ is a substituted hydrocarbon group, a substituted heterocyclic group, an unsubstituted hydrocarbon group, or an unsubstituted heterocyclic group, and
R$^4$ is an electron-withdrawing group.

2. The method of claim 1, wherein R$^1$ is a hydrocarbon group having a carbon number of 1 to 8.

3. The method of claim 1, wherein R$^2$ is a hydrocarbon group having a carbon number of 1 to 8.

4. The method of claim 1, wherein R$^3$ is a hydrocarbon group having a carbon number of 1 to 8 or a heterocyclic group having a carbon number of 1 to 8.

5. The method of claim 1, wherein the electron-withdrawing group is an alkoxycarbonyl group, an acyl group, an arylsulfonyl group, or an alkylsulfonyl group.

6. The method of claim 1, wherein the reacting is conducted in the presence of an optically active basic catalyst.

7. The method of claim 6, wherein the optically active basic catalyst is an optically active guanidine compound.

* * * * *